United States Patent
Petro

(10) Patent No.: US 6,436,292 B1
(45) Date of Patent: *Aug. 20, 2002

(54) PARALLEL HIGH-PERFORMANCE LIQUID CHROMATOGRAPHY WITH POST-SEPARATION TREATMENT

(75) Inventor: Miroslav Petro, Sunnyvale, CA (US)

(73) Assignee: Symyx Technologies, Inc., Santa Clara, CA (US)

(*) Notice: Subject to any disclaimer, the term of this patent is extended or adjusted under 35 U.S.C. 154(b) by 200 days.

This patent is subject to a terminal disclaimer.

(21) Appl. No.: 09/670,503

(22) Filed: Sep. 26, 2000

Related U.S. Application Data

(63) Continuation-in-part of application No. 09/285,363, filed on Apr. 2, 1999, now abandoned, and a continuation-in-part of application No. 09/285,393, filed on Apr. 2, 1999, now Pat. No. 6,265,226, and a continuation-in-part of application No. 09/285,333, filed on Apr. 2, 1999, now Pat. No. 6,260,407, and a continuation-in-part of application No. 09/285,335, filed on Apr. 2, 1999, now Pat. No. 6,175,409, and a continuation-in-part of application No. 09/285,392, filed on Apr. 2, 1999, now Pat. No. 6,294,388.
(60) Provisional application No. 60/157,338, filed on Oct. 1, 1999.

(51) Int. Cl.[7] .............................................. B01D 15/08
(52) U.S. Cl. ................... 210/656; 210/659; 210/143; 210/198.2; 73/61.52; 436/161; 422/70
(58) Field of Search ................ 210/635, 656, 210/659, 143, 198.2; 422/70; 436/161; 73/61.52

(56) References Cited

U.S. PATENT DOCUMENTS

| | | | |
|---|---|---|---|
| 4,532,043 A | 7/1985 | Prud'homme et al. | 210/656 |
| 4,629,566 A | 12/1986 | Prud'homme et al. | 210/656 |
| 4,711,764 A | 12/1987 | Good | 422/65 |

(List continued on next page.)

FOREIGN PATENT DOCUMENTS

| | | | |
|---|---|---|---|
| DE | 197 04 477 A1 | 8/1998 | 210/198.2 |
| EP | 0 675 356 B1 | 8/1997 | 210/198.2 |
| WO | WO 97/32208 | 9/1997 | 210/198.2 |

OTHER PUBLICATIONS

U.S. application No. 09/728,729, filed Nov. 28, 2000 Parallel Liquid Chromatography For Analyzing Combinatorial Libraries of Non–Biological Polymers pp. 1–184.*

Zeng et al., Anal. Chem. 70: 4380–4388 (1988). "Development of a Fully Automated Parallel HPLC/Mass Spectrometry System for the Analytical Characterization and Preparative Purification of Combinatorial Libraries".

Scholten et al., J. Chromatography 218: 3–13 (1981) "Fluorescence detection of chloroanilines in liquid chromatography using a post–column reaction with fluorescamine".

*Primary Examiner*—Ernest G. Therkorn

(57) ABSTRACT

High-performance liquid chromatography (HPLC) methods and systems are disclosed that combine parallel chromatographic separation of a plurality of samples with a detection technique that involves post-separation treatment of the plurality of samples to enhance one or more properties of the sample or of a component thereof, followed by detection of the one or more enhanced properties. Selective, tunable detection schemes are achievable, and are particularly advantageous as applied in connection with combinatorial chemistry, combinatorial material science and more particularly, combinatorial synthesis and screening of polymeric materials.

23 Claims, 14 Drawing Sheets

U.S. PATENT DOCUMENTS

| | | | |
|---|---|---|---|
| 4,980,130 A | 12/1990 | Metzger et al. | 422/70 |
| 5,071,547 A | 12/1991 | Cazer et al. | 210/198.2 |
| 5,334,310 A | 8/1994 | Frechet et al. | 210/198.2 |
| 5,443,791 A | 8/1995 | Cathcart et al. | 422/65 |
| 5,474,744 A | 12/1995 | Lerch | 422/100 |
| 5,492,831 A | 2/1996 | Ranger | 436/161 |
| 5,574,215 A | 11/1996 | Bunger et al. | 422/68.1 |
| 5,603,899 A | 2/1997 | Franciskovich et al. | 422/100 |
| 5,711,786 A | 1/1998 | Hinshaw | 95/82 |
| 5,766,481 A | 6/1998 | Zambias et al. | 210/656 |
| 5,783,450 A | 7/1998 | Yoshida et al. | 436/161 |
| 5,827,426 A | 10/1998 | Fujii et al. | 210/198.2 |
| 5,900,934 A | 5/1999 | Gilby et al. | 356/334 |
| 5,938,932 A | 8/1999 | Connelly et al. | 210/659 |
| 5,942,443 A | 8/1999 | Parce et al. | 436/514 |
| 6,040,186 A | 3/2000 | Lewis et al. | 422/100 |
| 6,054,047 A | 4/2000 | Hindsgaul et al. | 210/198.2 |
| 6,175,409 B1 * | 1/2001 | Nielsen | 356/387 |
| 6,260,407 B1 * | 7/2001 | Petro | 73/61.52 |
| 6,265,226 B1 * | 7/2001 | Petro | 436/180 |
| 6,294,388 B1 * | 9/2001 | Petro | 436/8 |
| 6,296,771 B1 * | 10/2001 | Petro | 210/656 |
| 6,345,528 B2 * | 2/2002 | Petro | 73/61.52 |

\* cited by examiner

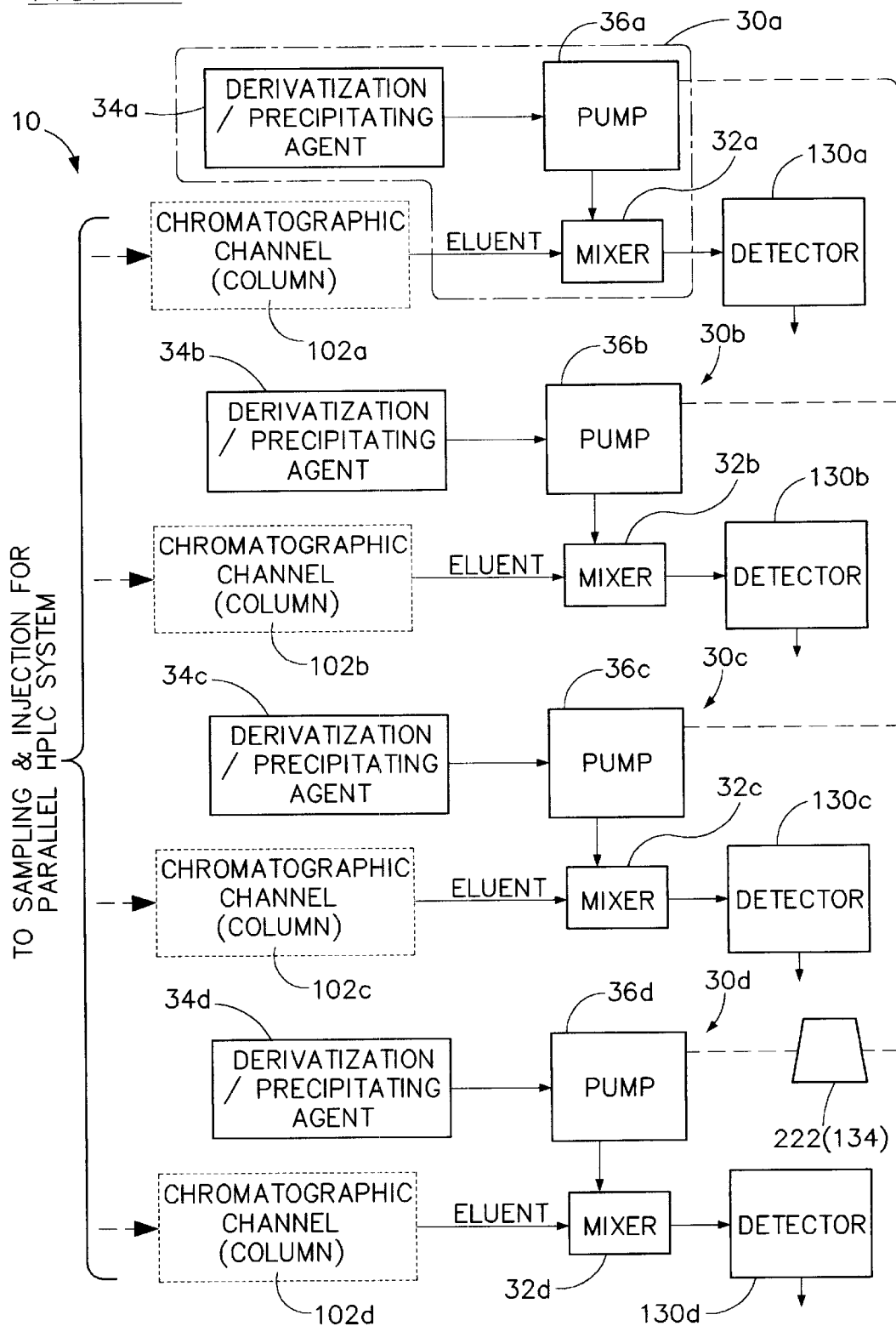

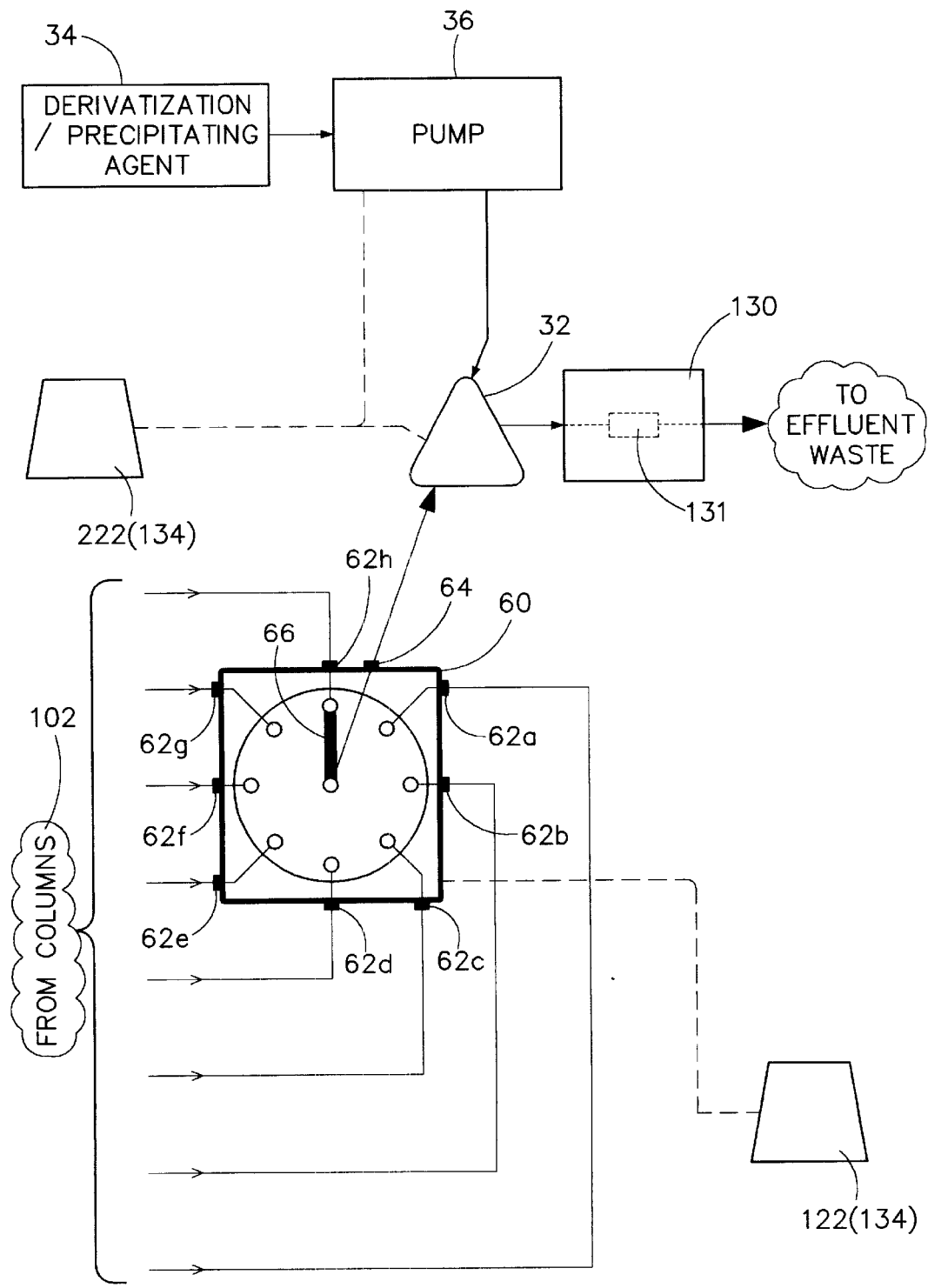

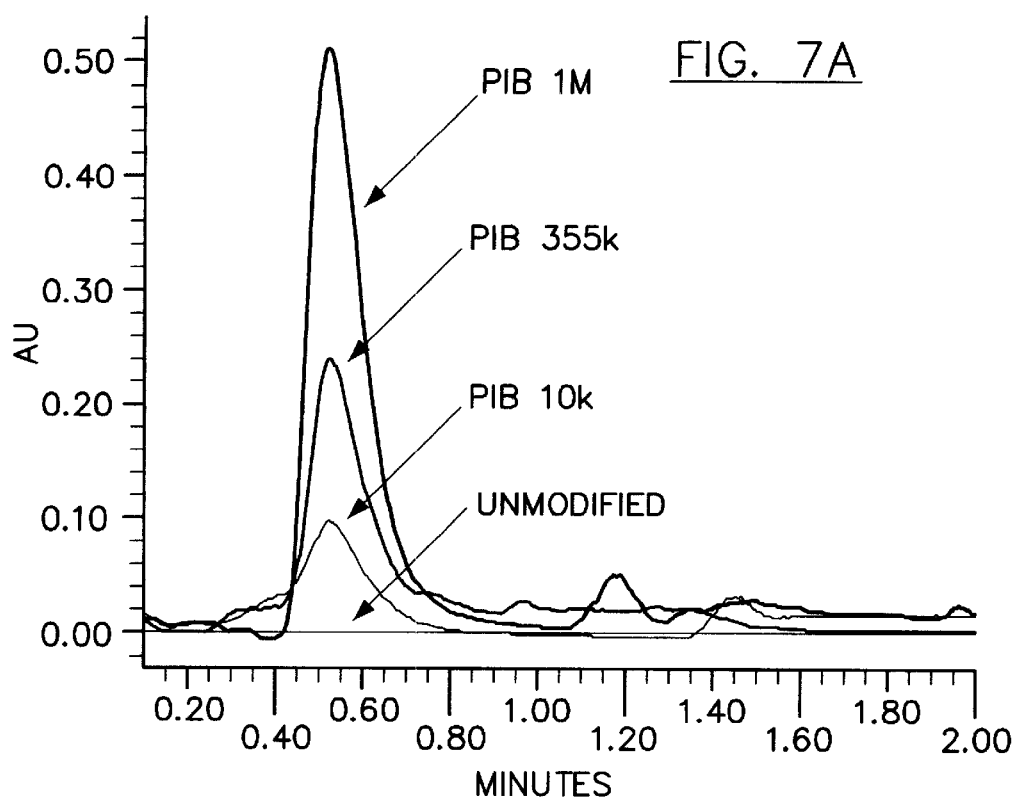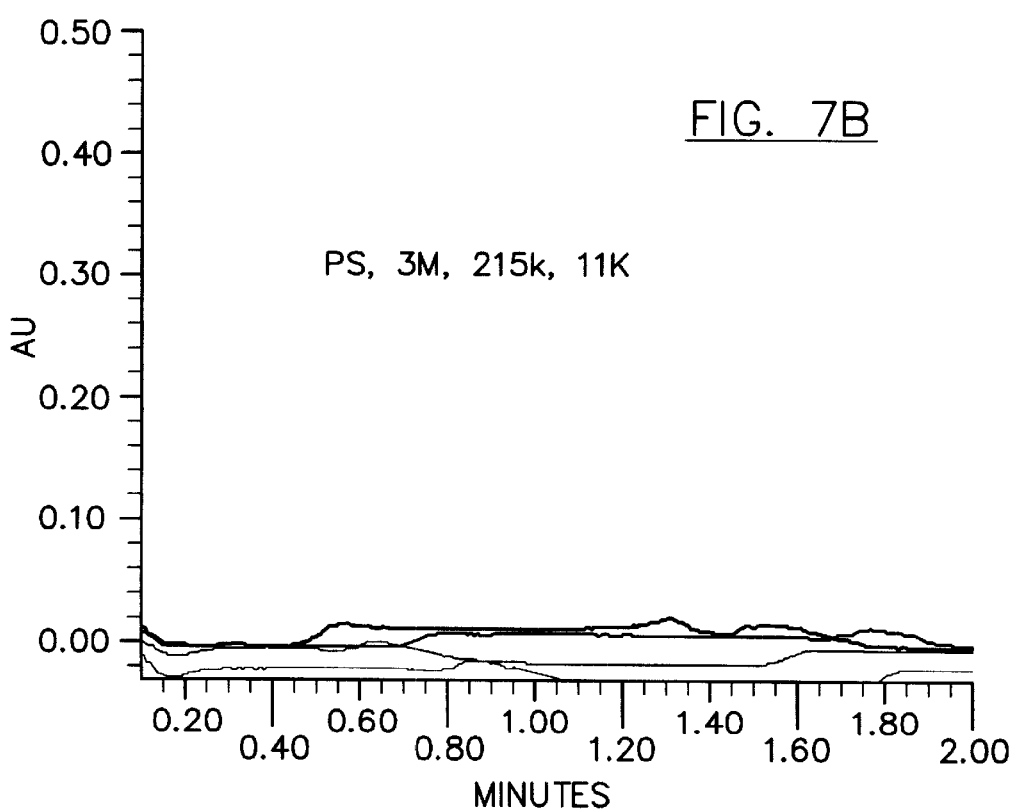

PARALLEL HIGH-PERFORMANCE LIQUID CHROMATOGRAPHY WITH POST-SEPARATION TREATMENT

This application claims priority to U.S. Provisional Application No. 60/157,338, filed Oct. 1, 1999 and the following continuation-in-part U.S. patent applications, each of which is hereby incorporated by reference for all purposes: Ser. No. 09/285,363 entitled "Rapic Characterization of Polymers", filed Apr. 2, 1999 by Petro et al., now abandoned; Ser. No. 09/285,393 entitled "Automated Sampling Methods for Rapid Characterization of Polymers", filed Apr. 2, 1999 by Petro et al. now now U.S. Pat. No. 6,265,226; Ser. No. 09/285,333 entitled "High-Temperature Characterization of Polymers", filed Apr. 2, 1999 by Petro et al. U.S. Pat. No. 6,260,407; Ser. No. 09/285,335 entitled "Flow-Injection Analysis and Variable-Flow Light Scattering Apparatus and Methods for Characterizing Polymers", filed Apr. 2, 1999 by Nielsen et al. now U.S. Pat. No. 6,175,409; and Ser. No. 09/285,392 entitled "Indirect Calibration of Polymer Characterization Systems", filed Apr. 2, 1999 by Petro et al. now U.S. Pat. No. 6,294,388. This application is related to U.S. patent application Ser. No. 09/410,546 entitled "Parallel High-Performance Liquid Chromatography With Serial Injection" filed by Petro et al. on Oct. 1, 1999, now U.S. Pat. No. 6,296,771, and is hereby incorporated by reference for all purposes.

BACKGROUND OF INVENTION

The present invention generally relates to liquid chromatography, and specifically, to high-pressure liquid chromatography (HPLC) methods for rapidly characterizing a plurality of samples. The invention particularly relates, in a preferred embodiment, to parallel HPLC methods for characterizing a combinatorial library comprising different polymers.

Liquid chromatography is generally well known in the art. High-pressure liquid chromatographic techniques involve injection of a sample into a mobile-phase that flows through a chromatographic column, separation of one or more components of the sample from other components thereof in the chromatographic column, and detection of the separated components with a flow-through detector. Approaches for liquid chromatography typically vary, however, with respect to the basis of separation and with respect to the basis of detection.

Gel permeation chromatography (GPC), a well-known form of size exclusion chromatography (SEC), is a frequently-employed chromatographic technique for separation of samples generally, and for polymer size determination particularly. Another chromatographic separation approach is illustrated by U.S. Pat. No. 5,334,310 to Frechet et al. and involves the use of a porous monolithic stationary-phase as a separation medium within the chromatographic column, combined with a mobile-phase composition gradient. Other separation approaches are also known in the art, including for example, normal-phase adsorption chromatography, and reverse-phase chromatography.

After separation, a detector can measure a property of the sample or of a sample component-from which one or more characterizing properties, such as molecular weight can be determined as a function of time. Specifically, with respect to polymer samples, for example, a number of molecular-weight related parameters can be determined, including for example: the weight-average molecular weight (Mw), the number-average molecular weight (Mn), the molecular-weight distribution shape, and an index of the breadth of the molecular-weight distribution (Mw/Mn), known as the polydispersity index (PDI). Other characterizing properties, such as mass, particle size, composition or conversion can likewise be determined. A variety of continuous-flow detectors have been used for measurements in liquid chromatography systems. Common flow-through detectors include optical detectors such as a differential refractive index detector (RI), an ultraviolet-visible absorbance detector (UV-VIS), or an evaporative mass detector (EMD)-sometimes referred to as an evaporative light scattering detector (ELSD). Additional detection instruments, such as a static-light-scattering detector (SLS), a dynamic-light-scattering detector (DLS), and/or a capillary-viscometric detector (C/V) are likewise known for measurement of properties of interest.

Detection methods involving post-separation treatment are known in the art. With respect to polymer samples, for example, European Patent EP 675 356 B1 to Staal discloses a method and a system for precipitating polymer components of a sample in the effluent stream from a chromatographic column, with optical detection of the precipitated components, and is hereby incorporated by reference for all purposes. Significantly, the application of such detection methods to parallel HPLC systems was not contemplated, and the benefits thereof were not heretofore appreciated in the art.

Broadly available liquid chromatography systems are not entirely satisfactory for efficiently screening larger numbers of samples. With respect to polymers, for example, high-performance liquid chromatographic techniques can typically take up to an hour for each sample to ensure a high degree of separation over the wide range of possible molecular weights (i.e., hydrodynamic volumes) for a sample. Notably, however, substantial improvements in sample throughput have been achieved in the art. For example, rapid-serial approaches for characterizing polymers have been developed by Symyx Technologies, Inc. (Santa Clara, Calif.) and disclosed in the aforementioned co-pending U.S. patent applications from which the present application claims priority. As another example, U.S. Pat. No. 5,783,450 to Yoshida et al. discloses rapid-serial protocols and systems for preparation, purification and separation of small molecules such as catecholamines and protaglandins from biological samples such as blood.

Parallel approaches for liquid chromatography have also been contemplated in the art. Zeng et al., Development of a Fully Automated Parallel HPLC/Mass Spectrometry System for the Analytical Characterization and Preparative Purification of Combinatorial Libraries, *Anal. Chem.* 70, 4380–4388 (1998), disclose analytical and preparative HPLC methods and systems involving the sequential preloading of samples onto two chromatographic columns, and then applying a mobile-phase in parallel to each of the columns to effect parallel separation of the samples. According to an alternative approach disclosed in U.S. Pat. No. 5,766,481 to Zambias et al., parallel separation of a plurality of molecules is effected by forming a mixture of selected, compatible molecules, and subsequently resolving the mixture sample into its component molecules by separation in a single-channel HPLC system. Parallel approaches have likewise been employed in other separation protocols, such as capillary electrophoresis. See, for example, U.S. Pat. No. 5,900,934 to Gilby et al.

Although such parallel approaches and systems have been generally contemplated, there nonetheless exists a need in the art for improving such approaches and systems with respect to overall sample throughput and/or quality of data.

Moreover, with the development of combinatorial materials science techniques that allow for the parallel synthesis of libraries comprising a vast number of diverse industrially relevant materials, and especially polymeric materials, there is a need for HPLC methods and systems to rapidly characterize the properties of samples from such combinatorial libraries.

SUMMARY OF INVENTION

It is therefore an object of the present invention to provide HPLC systems and protocols having a higher overall sample throughput, and in preferred applications, employing such systems and protocols for characterizing combinatorial libraries of material samples such as polymer samples, and particularly, libraries of or derived from polymerization product mixtures, to facilitate the discovery of commercially important materials such as polymeric materials, catalysts, polymerization conditions and/or post-synthesis processing conditions.

Briefly, therefore, the present invention is directed to methods and systems for characterizing a plurality of samples by liquid chromatography or, in some embodiments, by flow-injection analysis. According to the methods, a mobile phase is supplied in parallel through each of first and second chromatographic columns of a high-pressure liquid chromatography system. First and second samples are injected into the mobile phase of the first and second chromatographic columns, respectively. In chromatographic applications, at least one sample component of the injected first and second samples is separated from other sample components thereof in the respective chromatographic columns. Significantly, after separation, but before detection, at least one separated sample component of the first and second samples is treated to change a property of at least one separated sample component thereof. The treatment is preferably precipitation and/or derivitization. A property of the treated sample component of the first and second samples is detected.

The present invention provides substantial advantages over known approaches for parallel liquid chromatography systems. High overall throughput is achieved with a parallel HPLC system—even for samples (e.g., many types of polymers) having components that would otherwise be difficult to detect, and moreover, in a cost-effective manner. These advantages are particularly realized in preferred embodiments, in which optical detectors are employed. Moreover, methods of the invention can be advantageously employed in connection with mini- and micro-scale parallel liquid chromatography systems, since optical detectors are readily miniaturized—even to macro-scale applications.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIG. 2A through FIG. 2C are schematic diagrams illustrating embodiments for the application of post-separation treatment to parallel HPLC systems having four chromatographic channels and four dedicated parallel detectors (FIG. 2A and FIG. 2B) or a single detector with a detection switching valve (FIG. 2C).

FIG. 7A and FIG. 7B are graphs of detector output (mv, absorbance at 350 nm) versus time (minutes) illustrating the results from a HPLC separation of narrow polydispersity polyisobutylene (PIB) standards (FIG. 7A) and narrow polydispersity polystyrene (PS) standards (FIG. 7B) of various molecular weights (PIB at 1M, 355 k and 10 K; and PS at 3 M, 215 k and 11 k) each in a tetrahydrofuran mobile phase/eluant, run: (i) without treatment of the chromatographic column effluent (unmodified control) and (ii)with treatment of the chromatographic column effluent with water at a flow rate of 0.1 ml/min (See Example 2).

DETAILED DESCRIPTION OF THE INVENTION

In the present invention, methods and apparatus having features that enable an effective combinatorial materials research program are provided. Such a research program may be directed, for example, to identifying or optimizing commercially valuable polymers, catalysts or other materials, or to other research goals, such as process characterization and optimization. Other applications, including parallel industrial process monitoring or control are also enabled by the present invention.

Sample characterization approaches and systems of the invention involve parallel HPLC approaches and systems combined with post-separation treatment protocols and systems. Specifically, a plurality of samples are separated in parallel in two or more chromatographic columns, and the samples and/or one or more separated components thereof are subsequently treated, for example with a precipitating or derivatizing agent, to change one or more properties of the one or more components—for enhanced and/or selectively enhanced detection of such property or properties. In preferred approaches, the treatment effects a change in an optical property, and the detected property of the treated sample and/or component is an optical property.

The present invention is preferably applied to, and primarily discussed in connection with, combinatorial chemistry, combinatorial material science and more particularly, combinatorial synthesis and screening of polymeric materials. Briefly, in a combinatorial approach for identifying or optimizing materials (e.g., polymers) or reaction conditions, a large compositional space (e.g., of monomers, comonomers, catalysts, catalyst precursors, solvents, initiators, additives, or of relative ratios of two or more of the aforementioned) and/or a large reaction condition space (e.g., of temperature, pressure and reaction time) may be rapidly explored by preparing libraries of diverse materials and then rapidly screening such libraries. Combinatorial polymer libraries can comprise, for example, reaction product mixtures resulting from reactions that are varied with respect to such factors. General aspects of combinatorial approaches for screening a library are discussed in more detail in connection with the above-identified patent applications to which the present invention claims priority. Hence, the invention can be applied to combinatorial chemistry and materials science involving polymers and other materials, as well as to more traditional HPLC applications. As such, the particular applications and sample materials disclosed herein are to be considered exemplary and non-limiting.

Parallel HPLC With Post-Separation Treatment

Figure 1A:
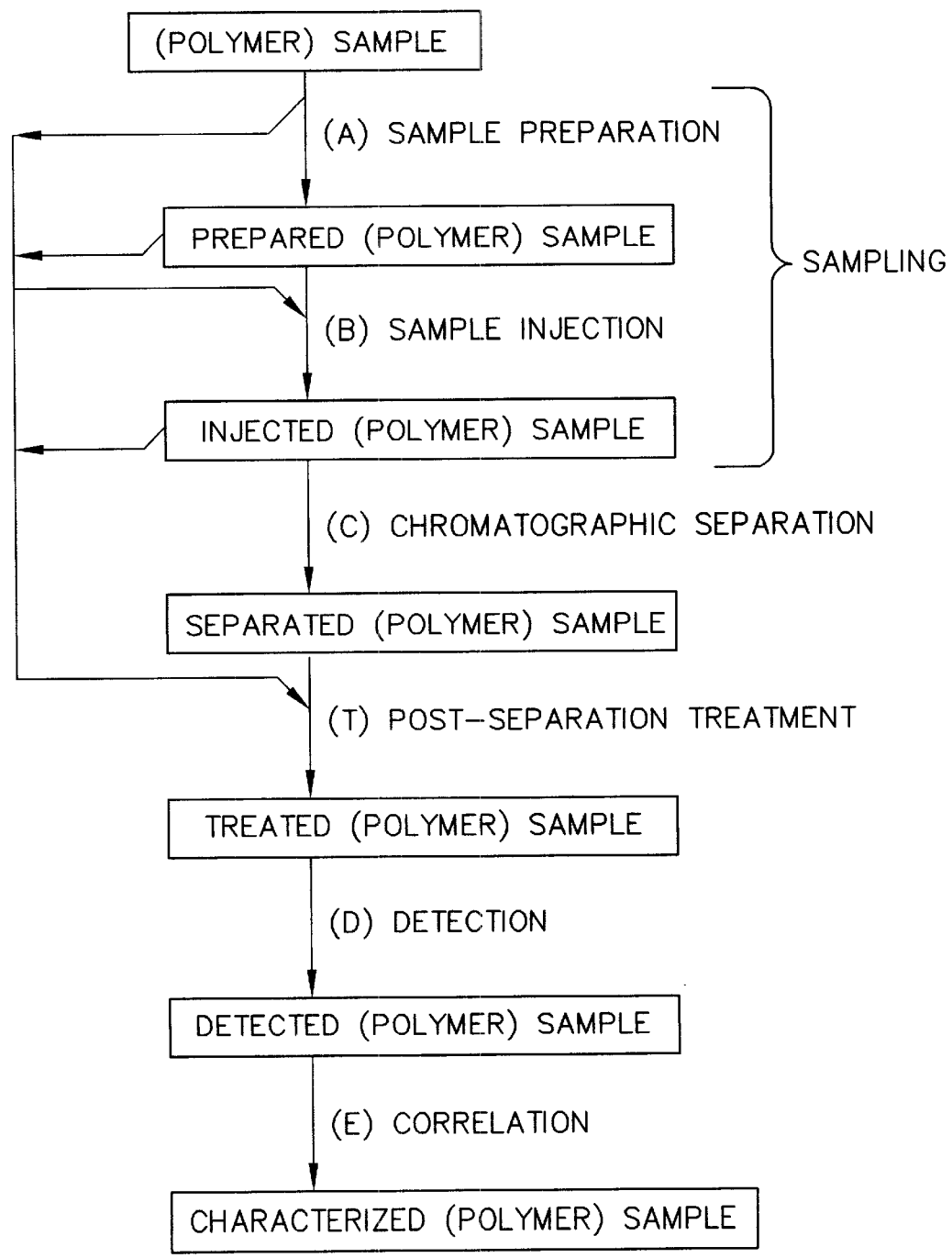
FIG. 1A through FIG. 1G are schematic diagrams showing an overview of polymer characterization process steps (FIG. 1A), a rapid-serial protocol for effecting such steps (FIG. 1B) for a plurality of samples ($s_1, s_2, s_3 \ldots s_n$) to obtain corresponding characterizing property information ($p_1, p_2, p_3 \ldots p_n$), a parallel protocol for effecting such steps (FIG. 1C) and several parallel-serial hybrid protocols for effecting such steps (FIG. 1D, FIG. 1E, FIG. 1F, and 1G).

With reference to FIG. 1A, characterizing a polymer sample according to the present invention using an HPLC system can include (A) preparing the sample (e.g., dilution), (B) injecting the sample into a mobile phase of a flow characterization system (e.g., liquid chromatography system, flow-injection analysis system), (C) separating the sample chromatographically, (T) treating the sample (e.g., with a precipitating agent or a derivatizing agent) to change a property (e.g., an optical property) of the sample or of a separated component thereof, (D) detecting a property of the polymer sample or of a component thereof, and/or (E) correlating the detected property to a characterizing property of interest. As depicted in FIG. 1A, various characterization protocols may be employed involving some or all of the aforementioned steps. The HPLC methods of the present invention involve injection generally include at least sample injection, chromatographic separation, treatment and detection (steps B, C, T and D).

Figure 1B:
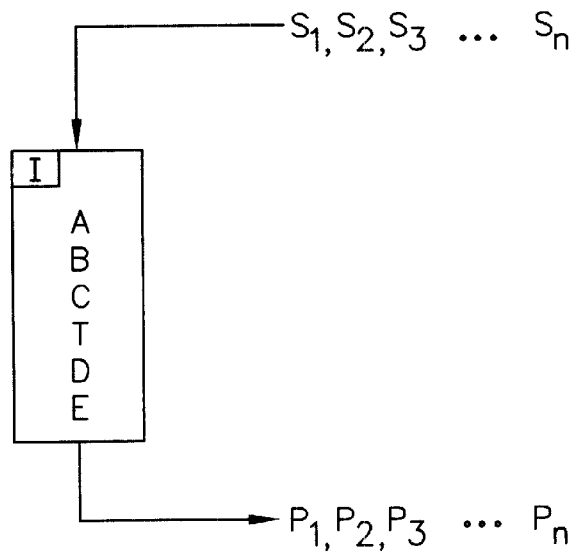

Prior art applications of post-separation treatment steps (e.g., precipitation) were effected in series with preceding separation steps and with subsequent detection steps in a single chromatographic channel (I). With reference to FIG. 1B, for example, a plurality of polymer samples can be characterized with a single polymer characterization system (I) in a traditional serial approach in which each of the plurality of polymer samples ($s_1, s_2, s_3 \ldots s_n$) are processed serially through the characterization system (I) with each of the steps (A, B, C, T, D, E) effected in series on each of the of samples to produce a serial stream of corresponding characterizing property information ($p_1, p_2, p_3 \ldots p_n$).

Figure 1C:
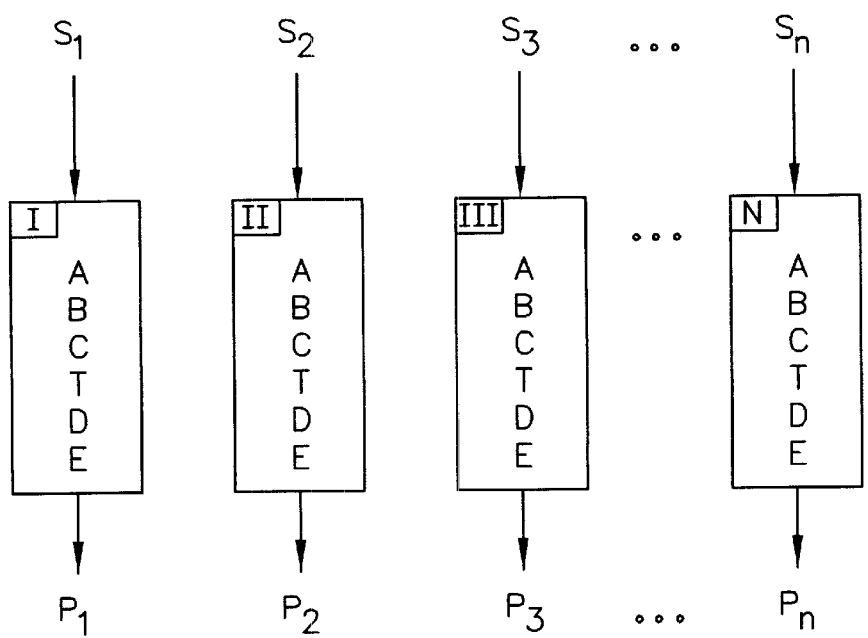

In contrast, the present invention is directed to parallel HPLC protocols and systems in which at least the chromatographic separation step (step C) is effected in a parallel manner (or in a staggered parallel manner, as disclosed, for example, in copending application Ser. No. 09/410,546, entitled "Parallel High-Performance Liquid Chromatography with Serial Injection", filed Oct. 1, 1999, by Petro et al. under Attorney Docket No. 99-79). With reference to FIG. 1C, for example, a plurality of polymer samples ($s_1, s_2, s_3 \ldots s_n$) can be characterized with two or more separate (or integrated) polymer characterization systems (or channels) (I, II, III . . . N) in a pure parallel (or for larger libraries, serial-parallel) approach in which the plurality of polymer samples ($s_1, s_2, s_3 \ldots s_n$) or a subset thereof are processed through the two or more polymer characterization systems (I, II, III . . . N) in parallel, with each individual system effecting each step on one of the samples to produce the characterizing property information ($p_1, p_2, p_3 \ldots p_n$) in parallel.

In a hybrid, parallel-series approach, certain of the steps of the characterization process can be effected in parallel, while certain other steps can be effected in series. Preferably, for example, it may be desirable to effect the longer, throughput-limiting steps (e.g., separation) in parallel for the plurality of samples, while effecting the faster, less limiting steps in series. Such a parallel-series hybrid approach can be exemplified, with reference to FIG. 1D, by parallel sample preparation (step A) of a plurality of polymer samples ($s_1, s_2, s_3 \ldots s_n$), followed by serial injection (step B), and then parallel chromatographic separation, treatment, detection and correlation (steps C, T, D and E) to produce a parallel stream of corresponding characterizing property information ($p_1, p_2, p_3 \ldots p_n$). In another exemplary parallel-series hybrid approach, represented schematically in FIG. 1E, a plurality of polymer samples ($s_1, s_2, s_3 \ldots s_n$) are prepared and injected in series into the mobile phase of four or more liquid chromatography characterizing channels (I, II, III . . . N), and then separated, treated, detected and correlated in a slightly offset (staggered) parallel manner to produce the characterizing property information ($p_1, p_2, p_3 \ldots p_n$) in the same staggered-parallel manner. If each of the separation and detection systems has the same processing rates, then the extent of the parallel offset (or staggering) will be primarily determined by the speed of the serial preparation and injection. In a variation of the preceding example, with reference to FIG. 1F, where the detection and correlation steps are sufficient fast, a plurality of polymer samples ($s_1, s_2, s_3 \ldots s_n$) can be characterized by serial sample preparation and injection, staggered-parallel chromatographic separation and treatment (steps C and T), and then serial detection and correlation, to produce the characterizing property information ($p_1, p_2, p_3 \ldots p_n$) in series. In this case, the rate of injection into the various separation columns is preferably synchronized with the rate of detection. In an additional variation of the preceding example, with reference to FIG. 1G, a plurality of polymer samples ($s_1, s_2, s_3 \ldots s_n$) can be characterized by serial sample preparation and injection, staggered-parallel chromatographic separation (step C), and then serial treatment, detection and correlation (steps T, D and E), to produce the characterizing property information ($p_1, p_2, p_3 \ldots p_n$) in series.

The parallel and parallel-hybrid approaches, with post-separation treatment, can be used with one or more of the several rapid-serial optimization approaches—directed toward optimization of one or more characterization steps (e.g., steps (A) through (E) of FIG. 1A) with respect to speed and quality of information—that are disclosed in the above-identified patent applications to which the instant application claims priority.

Figure 2B:
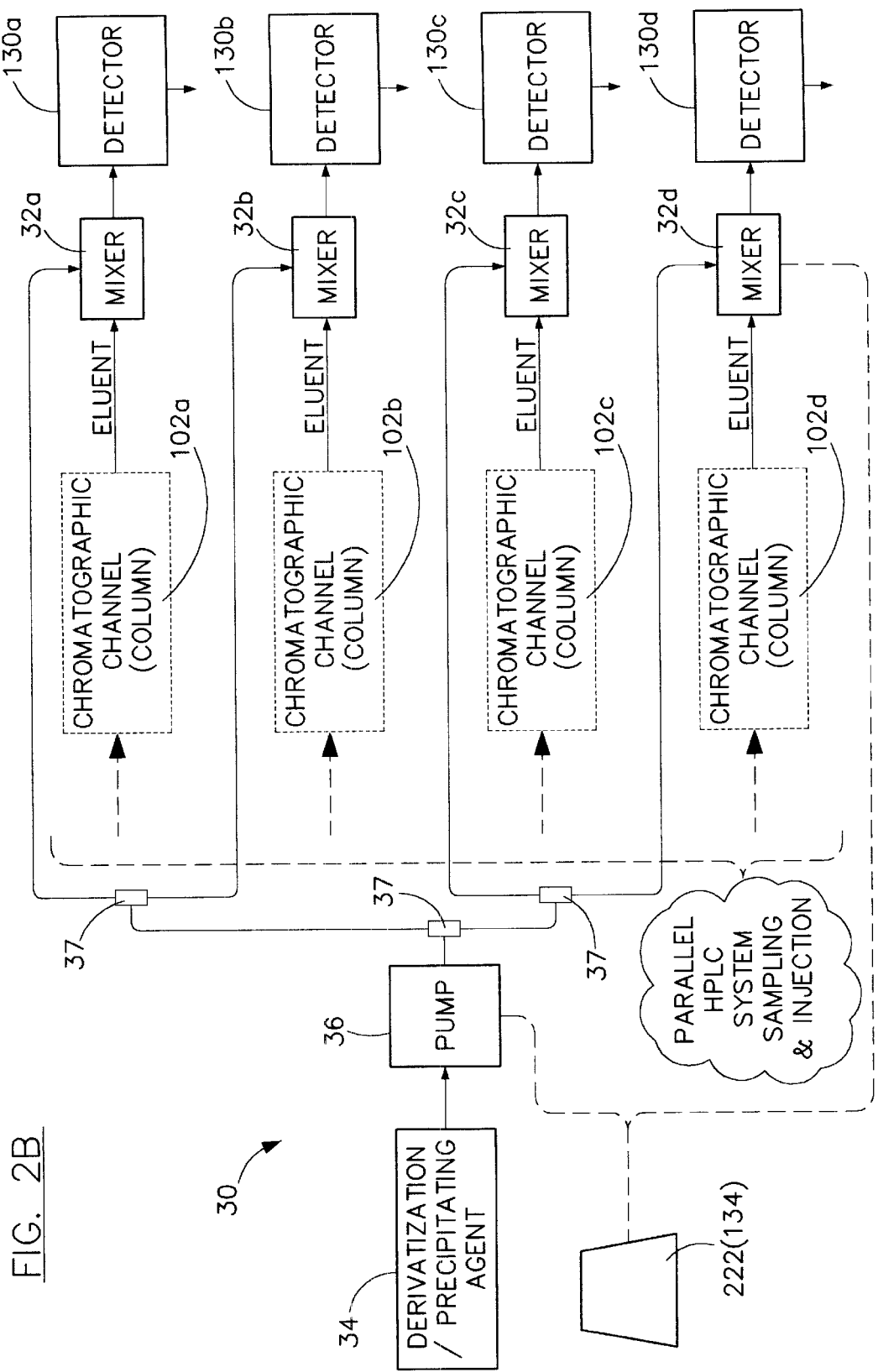

The parallel HPLC system of the present invention comprises a detection system that includes means for treating sample components in parallel chromatographic column eluants. With reference to FIG. 2A through FIG. 2C, for example, such detection system can include one or more treatment systems 30 comprising a treatment agent reservoir 34, a treatment pump 36 and a mixer such as an in-line mixer 32 with appropriate connecting conduits and valving to provide fluid communication between the treatment agent reservoir 34 and the mixer 32. As shown in FIG. 2A, the HPLC system can include parallel treatment systems for each parallel chromatographic channel. Specifically, two or more treatment systems 30a, 30b, 30c, 30d that are each dedicated to a particular chromatographic channel (with each channel including one or more column(s) 102a, 102b, 102c, 102d). Parallel treatment for parallel chromatographic channels can also be acheived, with reference to FIG. 2B, in an alternative embodiment in which the treatment system 30 can include one treatment agent reservoir 34 with associated treatment pump 36 serving two or more mixers 32a, 32b, 32c, 32d with appropriate flow-splitters 37 (e.g., "T"-connectors), conduits and valving to provide fluid communication between the treatment agent reservoir and the two or more mixers 32. According to another approach, with reference to FIG. 2C, the sample components of parallel chromatographic channel eluants can be treated in series, with a single mixer 32, by routing the two or more channel eluants through a detection switching valve 60 for selective, serial delivery to the mixer 32. Briefly, the detection switching valve 60 will have two or more selectable inlet ports, 62a through 62h, and at least one outlet port 64. The inlet ports 62 are in fluid communication with two or more chromatography channels (columns), and additionally, are selectable in fluid communication with the outlet ports 64. Switch 66 can be used to selectively connect one of the inlet ports 62 with the outlet port 64. The outlet port 64 is itself in fluid communication with the mixer 32 of the treatment system 30. The switch 66 of the detection valve 60 can be manually or automatically actuated, and is preferably under microprocessor 122 (134) control. The mixer 32 can be supplied with one or more treatment agents from one or more treatment reservoirs 34 by one or more treatment pumps 36.

The post-separation treatment of the present invention can be any treatment that changes a property of at least one of the separated sample components of the first and second samples. Preferably, the treatment is selective to one or more particular sample components of interest. Precipitation and derivitization are preferred post-separation treatment protocols. Preferably, the sample components of the first and second (or more) samples are precipitated and/or derivatized—after separation but before detection—to make them more susceptible or to make them selectively detectable to detection, and most preferably, to optical detection.

Post-separation precipitation can be effected by any suitable means. The treatment can be effected, for example, by combining the chromatographic eluant with a treatment agent—such as a precipitating agent or derivatizing agent (e.g., in a mixer). Preferably, the composition, flow-rate and/or temperature of the post-separation column eluant is controlled to selectively precipitate the one or more sample components of interest. Most preferably, a non-solvent for the component of interest is combined with the column eluant at various flowrates for selective precipitation. See Examples 1 through 4. See also European Patent EP 675 356 B1, which is incorporated by reference in its entirety for all purposes.

Derivitization can include any type of derivitizing chemical reaction known in the art that results in a product that has properties different from the reactant sample component. The selective oxidation of an alcohol to the corresponding ketone is exemplary. Other derivitizing agents are known in the art for incorporating markers, labels (e.g., fluorescent compounds, radioactive elements or compounds, dyes, etc.)

Advantageously, such protocols can be cost-effectively applied in combination with parallel optical detectors, and moreover, such combination can be efficiently and suitable applied in mini- and micro-scaled liquid chromatography systems. As noted below, such mini- and micro-scale liquid chromatography systems can be advantageously applied in connection with combinatorial chemistry and materials science research.

The particular configuration for the parallel chromatographic separation and/or parallel chromatographic channels with which the aforementioned post-separation treatment protocols/treatment systems are employed is not narrowly critical. In general, the parallel chromatography can include pure parallel configurations as well as hybrid parallel-series configurations, as described above. As used herein, parallel chromatographic separation/channels means that chromatographic separation of at least two or more samples is effected in at least two or more channels, respectively. The separation is at least partially overlapped (simultaneous separation), although initiation and conclusion times may differ. Additionally, and particularly as applied to combinatorial chemistry and materials science applications, parallel chromatographic separation of a subset of the total number of samples being evaluated can be particularly advantageous.

Figure 3A:
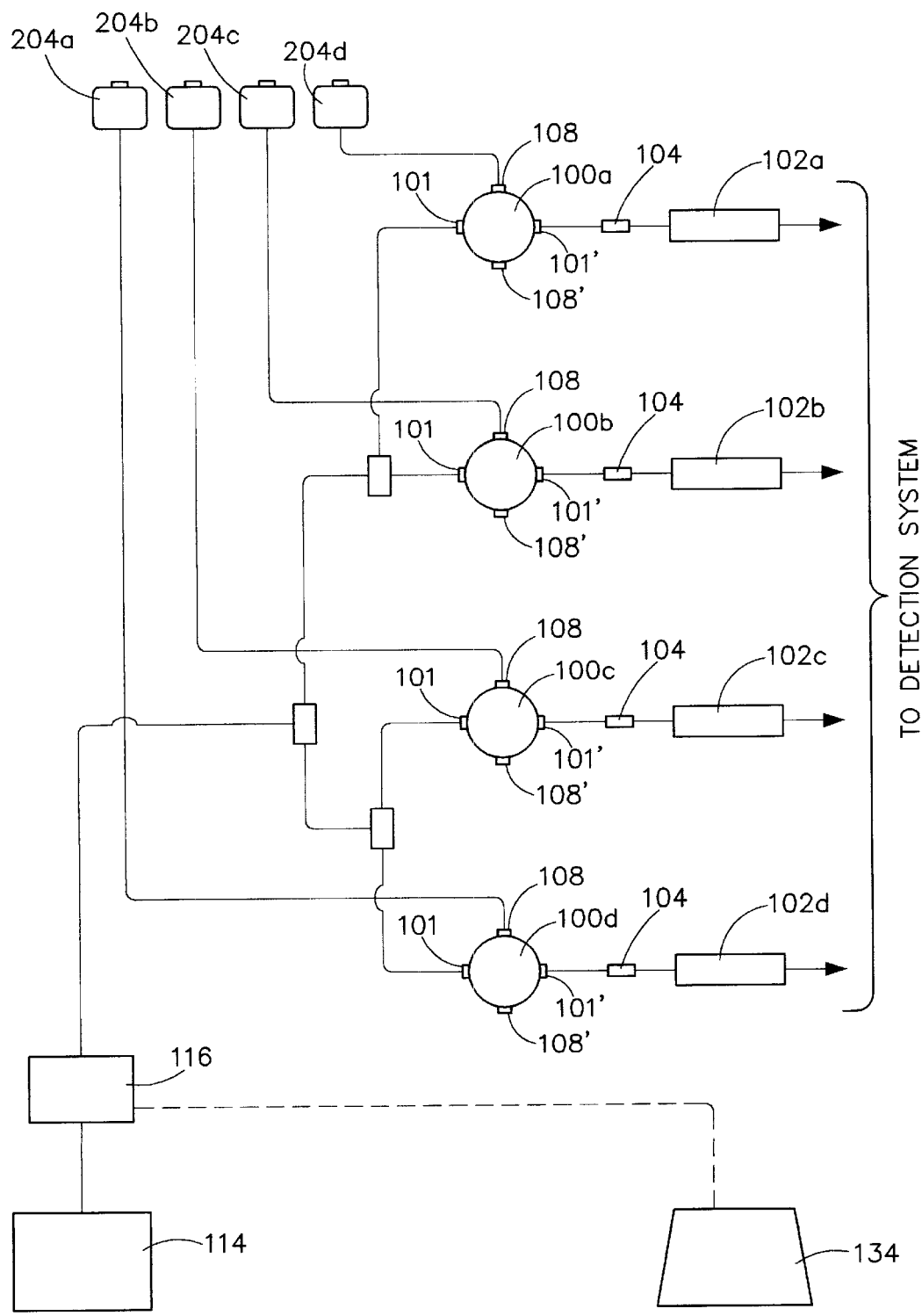
FIG. 3A and FIG. 3B are schematic diagrams illustrating various parallel high-performance liquid chromatography systems as embodiments of the invention having four chromatographic channels with four dedicated sample loading ports and injection valves (FIG. 3A) or a single sample loading port and single injection valve with a multi-port switching valve (FIG. 3B).

FIG. 3A shows one embodiment of a parallel chromatography system. The system comprises two or more chromatographic columns 102a, 102b, 102c, 102d into which a mobile phase is supplied in parallel through an injection valve 100a, 100b, 100c, 100d, respectively, by HPLC pump 116 from a mobile phase reservoir 114, via appropriate flow-splitters, conduits and valving. A plurality of samples can be loaded into the injection valves 100 through sample loading ports 204a, 204b, 204c, 204d. The samples can be loaded in parallel, or alternatively, in a stepped serial fashion. In operation, a mobile phase is supplied in parallel from the reservoir 114 to each of the columns 102, and samples are injected into the mobile phases through injection valves 100. Following injection, the injected samples are optionally filtered with in-line filters 104 and one or more sample components are then chromatographically separated from the sample and/or from other sample components thereof. The separated samples/sample components can then be delivered to the detection system for treatment and subsequent detection (e.g., according to one of the embodiments discussed above).

Figure 3B:
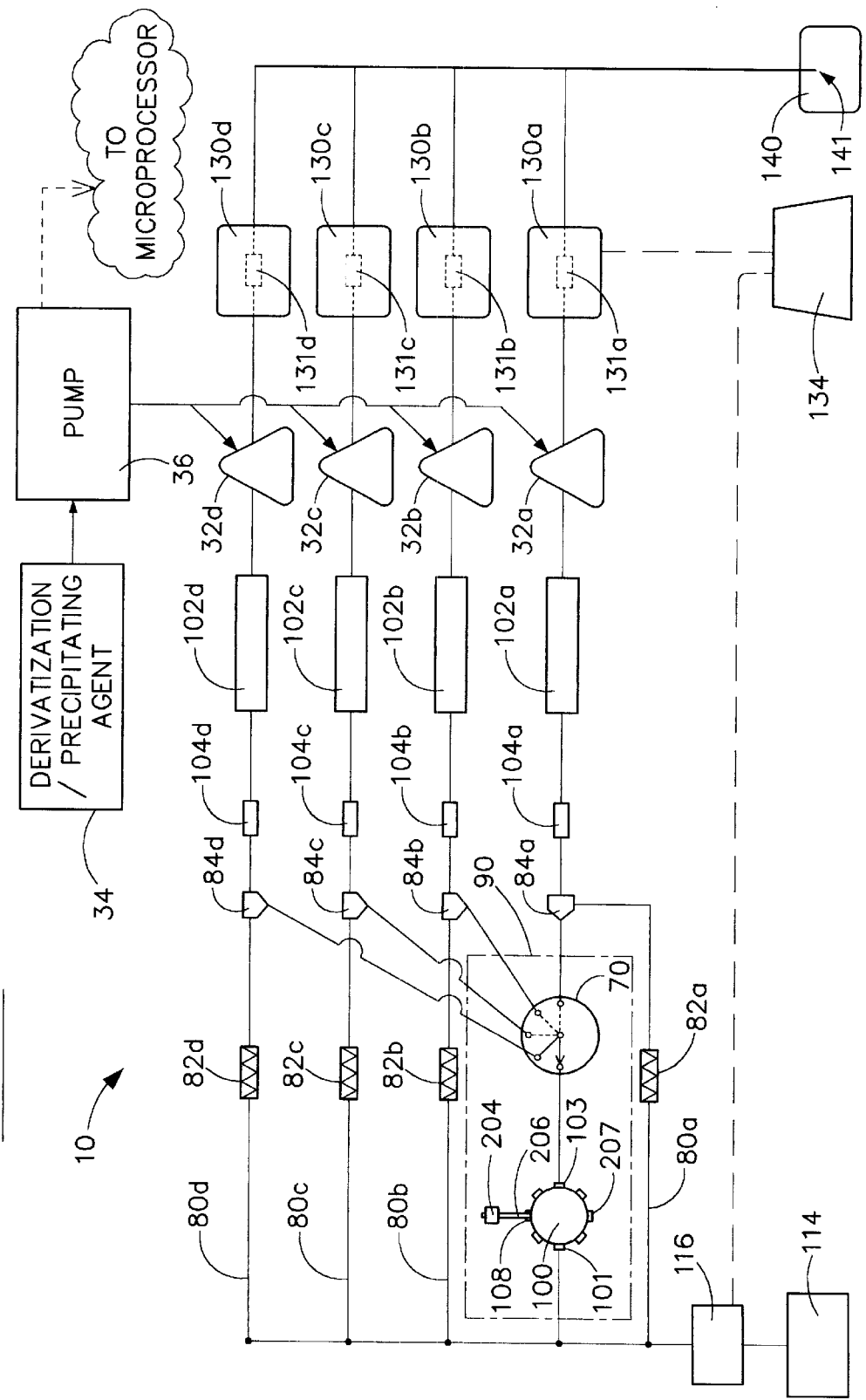

One embodiment of a preferred hybrid parallel-serial chromatographic separation approach and system (with serial injection) is shown in FIG. 3B, and discussed in greater detail in U.S. patent application Ser. No. 09/410,546, now U.S. Pat. No. 6,296,771 entitled "Parallel High-Performance Liquid Chromatography With Serial Injection" filed by Petro et al. on Oct. 1, 1999. Briefly, the parallel HPLC system with serial injection 10 can comprise a sample injection system 90 for serially and distributively injecting a plurality of samples into a liquid mobile phase supplied in parallel to each of two or more chromatographic columns 102a, 102b, 102c, 102d. The injection system comprises an injector and a multi-port switching valve. The injector, which is preferably an injection valve 100 such as are typically employed in single-channel HPLC systems, provides a motive force for injecting a sample under pressure into the mobile phases being supplied to the two or more chromatographic columns. The multi-port switching valves provides sequential distribution of the samples to the mobile phases. At least one sample component of the plurality of injected samples are separated from other sample components thereof in the respective chromatographic columns 102a, 102b, 102c, and 102d, and a property of at least one of the separated sample components is treated in the mixer 32a, 32b, 32c, 32d, and then detected in one or more flow-through detectors 130a, 130b, 130c, 130d. The liquid mobile phase is supplied in parallel to the chromatographic columns 102a, 102b, 102c, 102d from a mobile-phase source through two or more column supply conduits 80a, 80b, 80c, 80d, which can also in-line pressure reducers 82a, 82b, 82c, 82d (e.g., flow restrictors), respectively, and in-line injection connectors 84a, 84b, 84c, 84d, respectively. The reservoir(s) 114 can be of any suitable design and capacity, and typically have a volume of about 4 liters. The one or more pumps 116 can be of any type and size suitable to provide a motive force for the mobile-phase fluid through the systems 10. After passing through the chromatographic columns 102a, 102b, 102c, 102d and detectors 130a, 130b, 130c, 130d, the mobile phase is discharged from the system via a common discharge header and effluent port 141 into a waste collection container 140. Variations in this embodiment, as well as other embodiments for such parallel-serial approach are disclosed in the referenced co-pending application. Regardless of the particular configuration of the parallel chromatographic system and/or of the treatment and detection systems, the internal system pressures (e.g., mobilephase pressures) delivered by the HPLC pump are typically at least about 100 psig, at least about 200 psig, at least about 500 psig or at least about 1000 psig. Higher pressures, up to several thousand psig, can also be employed in robust systems. Hence, the pump pressures can range from about 100 psig to about 6000 psig, from about 200 psig to about 4000 psig, from about 500 psig to about 4000 psig, and from about 1000 psig to about 4000 psig. Typical high-pressure liquid chromatography pumps, available commercially from various sources, such as Waters Model No. 515 (Milford, Mass.) can be employed. The one or more pumps 116 can be controlled with one or more microprocessors 134. In operation, pump pressures can vary substantially depending on the particular configuration of the system 10, including for example the number of chromatographic columns 102, the separation media employed therein, the desired flowrates, the desired robustness, etc.

Figure 4:
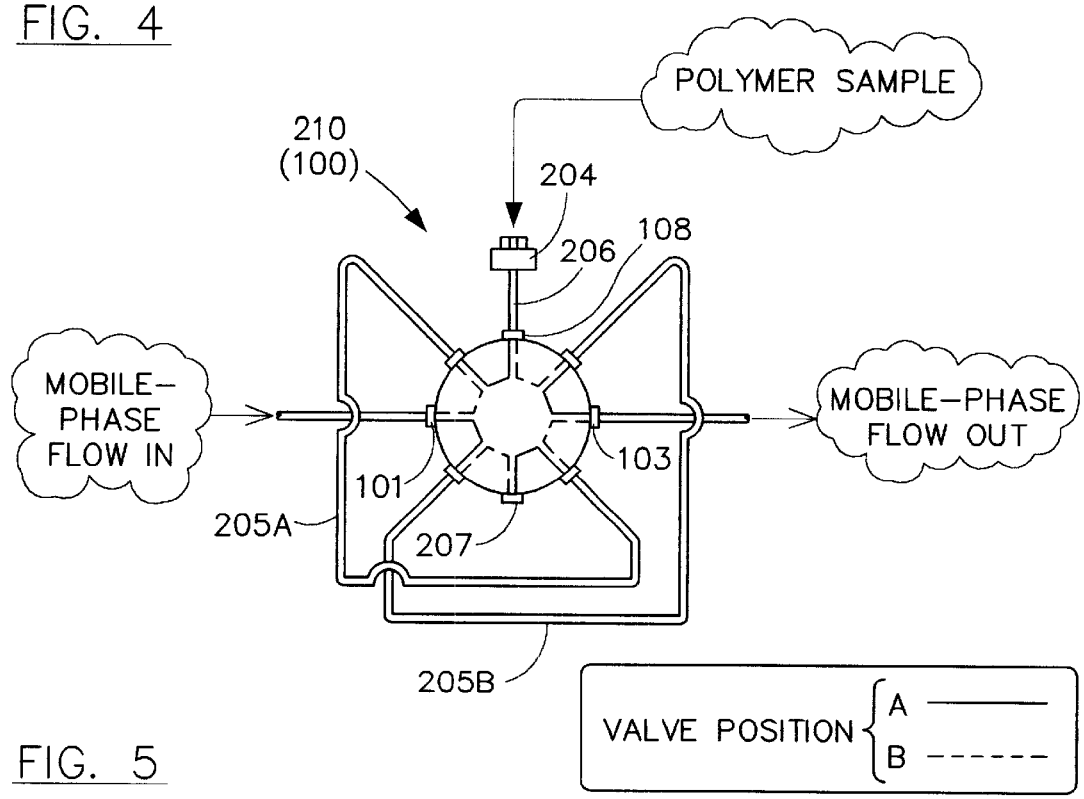
FIG. 4 is a schematic diagram illustrating an eight-port injection valve that can be used (e.g., in connection with a multi-port switching valve) for loading a polymer sample and for injection thereof into a mobile phase of a flow characterization system.
Figure 5:
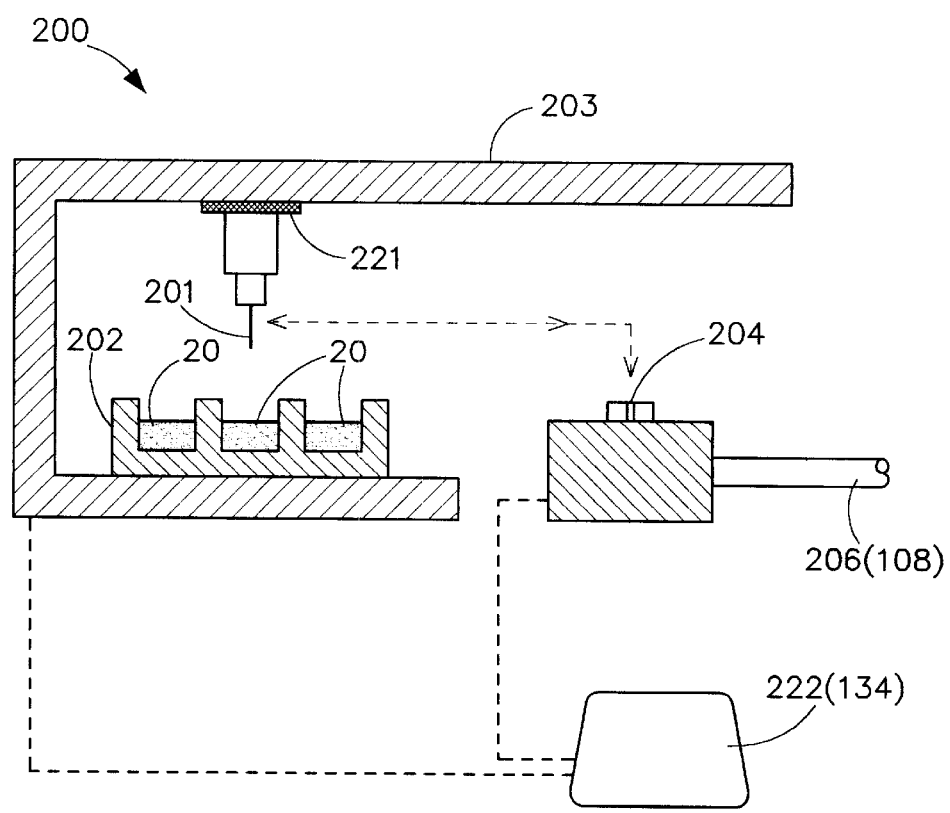
FIG. 5 is a schematic diagram illustrating an automated sampling system.

With reference to FIG. 4, a preferred injection valve 100 for use in connection with the parallel HPLC systems of the invention can be an 8-port, two-loop injection valve 210 (100) that operates as follows. A first sample is loaded directly into an injection port 108 or indirectly through a loading port 204, transfer line 206 and the injection port 108 at relatively low pressure compared to the pressure of the mobile phase. The loading port 204 can be adapted in size to accommodate one or more injection probes (tips) of a manual or an automated sample delivery unit (e.g., an auto-sampler). When the 8-ported valve is in valve position "A" (with internal flow-paths for the valve indicated by solid lines), the first sample is loaded into a sample loop 205A while the mobile phase flows through the valve via mobile-phase inlet port 101 (the flow-in port), sample loop 205B, and mobile-phase outlet port 103 (the flow-out port). The sample loops 205A and 205B can be of equal volume or of varying volume. A waste port 207 can be employed for receiving any overflow sample and/or for flushing the valve after each sample, if necessary. When the injection valve 210 is switched to the valve "B" position (with internal flow-paths for the valve now indicated by the dashed lines), the mobile phase then flows through the valve via mobile-phase inlet port 100, sample loop 205A, and mobile-phase outlet port 103, and the first sample is thereby injected, via the multi-port switching valve, into the mobile phase of one of the chromatographic columns 202 of the liquid chromatography system 10. The mobile-phase outlet port 103 is the sample-discharge port of the injection valve when a sample is present in the mobile phase. While the first sample is being injected from sample loop 205A into the first mobile phase, a second sample can be loaded into sample loop 205B, ready to be injected once the injection valve 100 is switched back to valve position A, and the multi-port switching valve is switched to provide a path of fluid communication to the mobile phase of a second chromatographic column. Eight-ported valves, such as represented in FIG. 3, can be purchased from Valveco Instruments Co. Inc. (Houston, Tex.), and the purchased valve fittings can be modified as described above for use in connection with a flow characterization system. An eight port injection valve 210 is a preferred injection valve 100 because the two sample loops 205A, 205B allow the flow characterization system to be ready for sample loading at all times (i.e., has a load/load capability). As such, the eight-port valve is faster than, for example, a six port valve (e.g., a valve having only a single load position and a single inject position), and therefore, the eight-port injection valve provides one aspect for improving the sample throughput for a liquid chromatography system 10 or a flow-injection analysis system 20. While the eight-port valve 210 depicted schematically in FIG. 4 is a preferred configuration, other high-pressure injection valves can also be suitably employed, including, without limitation, valves having a greater or lesser number of ports. Typically, however, a high-pressure injection valve will have from 6 to 24 ports.

While the aforementioned embodiment is preferred, the particular design of the injection valve is not critical. The injection valve 100 (210) can be configured, for example, to have more than one injection port 108, a single injection port 108, and in either case, the single or multiple injection ports 108 be in fluid communication with a number of loading ports 204 via a number of transfer lines 206 in order to receive samples independently from a number of different injection probes, including, for example, a manual injection probes, and one or more probes associated with automated delivery systems, such as one or more robotic auto-samplers. The injection valve can also have a larger number of sample loops with the same or with varying volumes, to accommodate different samples sizes.

Sample loading into the injection system, also referred to herein as "sampling", can be effected in any suitable manner, and the particular manner employed is not critical to the invention. Sampling of a sample generally refers to a plurality of steps which include withdrawing a polymer sample from a sample container and delivering at least a portion of the withdrawn sample to the injection system of the HPLC system. Sampling may also include additional steps, particularly and preferably, sample preparation steps. (See FIG. 1A). In one approach, only one sample is withdrawn into the auto-sampler probe at a time and only one sample resides in the probe at one time. The one sample is expelled therefrom (for sample preparation and/or into the polymer characterization system) before drawing the next sample. In an alternative approach, however, two or more samples can be withdrawn into the auto-sampler probe sequentially, spatially separated by a solvent, such that the two or more samples reside in the probe at the same time. Such a "candystriping" approach can provide for very high auto-sampler throughputs for rapid introduction of the one or more samples into the flow characterization system.

The sample container from which the polymer sample is withdrawn is not critical. The sample container can be, for example a sample-containing well. The sample-containing well can be a sample vial, a plurality of sample vials, or a sample-containing well within an array of sample-containing wells (e.g., constituting a polymer sample library). The sample container can alternatively be a sample port from a sample line in fluid communication with an industrial process line, such as a polymerization process line.

In the general case, sampling can be effected manually, in a semi-automatic manner or in an automatic manner. A polymer sample can be withdrawn from a sample container manually, for example, with a pipette or with a syringe-type manual probe, and then manually delivered to a loading port or an injection port of a polymer characterization system. In a semi-automatic protocol, some aspect of the protocol is effected automatically (e.g., delivery), but some other aspect requires manual intervention (e.g., withdrawal of polymer samples from a process control line). Preferably, however, the polymer sample(s) are withdrawn from a sample container and delivered to the characterization system in a fully automated manner—for example, with an auto-sampler.

A plurality of samples, such as those included within a library of samples, is preferably delivered to the injection system (e.g., to injection valve 100 in FIG. 3A) for loading into the HPLC system, with an automatic delivery device, such as an auto-sampler. As used herein, the term "auto-sampler" refers to an apparatus suitable for automated sampling of polymer samples for characterization, including automated withdrawal of a polymer sample from a sample container, and automated loading of at least a portion of the withdrawn sample into an injection port or a loading port of a flow characterization system (e.g. a liquid chromatography system).

Automated sampling equipment is available commercially for introducing multiple samples into liquid flow systems in a serial manner. For example, autosamplers that can be suitably adapted for use in connection with the present invention are available from Gilson. While such commercially-available auto-sampling equipment could be used with this invention, improved autosamplers as disclosed in copending U.S. patent application Ser. No. 09/285, 393 entitled "Automated Sampling Methods for Rapid Characterization of Polymers", filed Apr. 2, 1999 by Petro et al. are preferably employed. Such autosamplers provide high-throughput, with substantial flexibility with respect to sample preparation, etc., and as such, are well suited to applications of the present invention to combinatorial materials science research.

Figure 6:
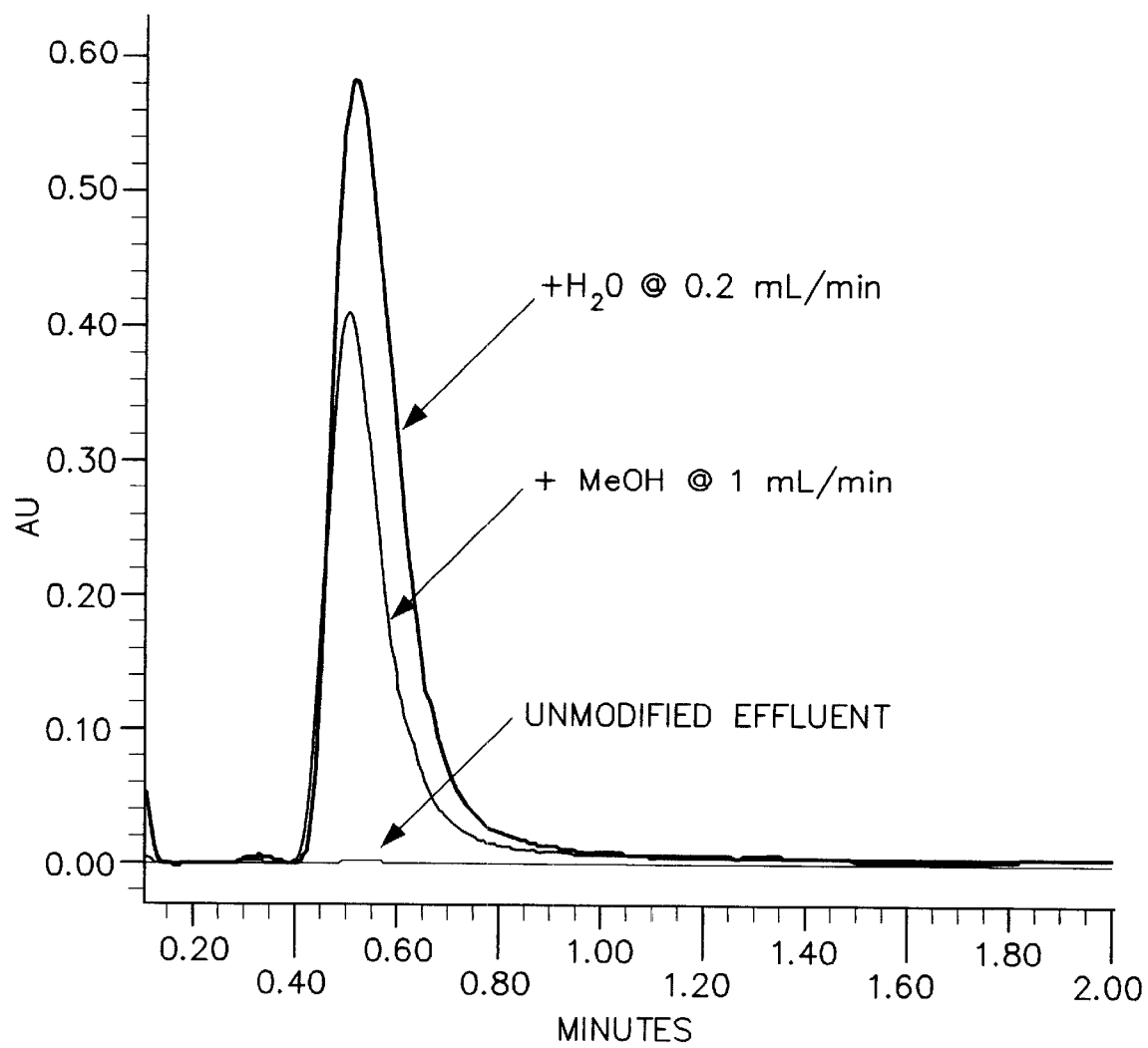
FIG. 6 is a graph of detector output (mv, absorbance at 350 nm) versus time (minutes) illustrating the results from a HPLC separation of narrow polydispersity polyisobutylene standard having a molecular weight of 1M in a tetrahydrofuran mobile phase/eluant, and run with various post-separation precipitation protocols: (i) without treatment of the chromatographic column effluent (unmodified control); (ii) with treatment of the chromatographic column effluent with methanol at a flow rate of 1 ml/min; and (iii) with treatment of the chromatographic column effluent with water at a flow rate of 0.2 ml/min (See Example 1).

Briefly, with reference to FIG. 6, in a preferred embodiment an auto-sampler 200 can comprise a movable probe (tip) 201, typically mounted on a support arm 203, a translation station 221 for providing three-dimensional motion of the probe, and a microprocessor 222 for controlling three-dimensional motion of the probe between various spatial addresses. The auto-sampler 200 preferably also comprises a user-interface (not shown) to allow for user programming of the microprocessor 222 with respect to probe motion and manipulations. The probe 201 can have an interior surface defining a sample-cavity and an inlet port for fluid communication between the sample cavity and a polymer sample 20. The probe 201 is also adapted for fluid communication with an injection port 108 (FIG. 2A, FIG. 2B) or a loading port 204 (FIGS. 2A, 2B) of the injection system 90. The support arm 203 is preferably an XYZ robotic arm, such as can be commercially obtained from Cavro Scientific Instruments, Inc. (Sunnyvale, Calif.) among others. To improve smoothness of operation at high speeds, such XYZ robotic arms preferably have motions based on gradient variations rather than step-function variations, and preferably are belt-driven rather than shaft driven. The microprocessor 222 can be a computer and can be the same or different from the microprocessor 134 (FIG. 2A, FIG. 2B) used to control the detectors 130 (FIG. 2A, FIG. 2B) and data acquisition therefrom. The auto-sampler can further comprise one or more pumps (not shown), preferably syringe pumps, for drawing and/or expelling liquids, and related connection lines (not shown) for fluid communication between the pumps, the probe 201, and liquid (e.g. solvent) reservoirs. Preferred embodiments include two or more syringe pumps—one with a relatively lower flowrate capacity and one with a relatively higher flowrate capacity. Alternative pump configurations, such as peristaltic pumps, vacuum-pumps or other motive-force providing means can be used additionally or alternatively. Sampling throughputs may also be enhanced by using two or more robotic arms together. It is likewise possible to have more two or more sample probes in connection with a single robotic arm—for example, such as an array of two or more probes each capable of synchronized motion relative to each other.

In operation, the microprocessor 222 of the auto-sampler 200 can be programmed to direct the auto-sampler 200 to withdraw a sample 20 (e.g., a polymer solution comprising a dissolved polymer) from a sample container (e.g., a sample well) formed in a sample tray 202 into the injection probe 201, and subsequently to direct the probe 201 to the loading port 204 for loading the sample into the characterization system through transfer line 206. In preferred embodiments, the auto-sampler can be programmed to automatically sample each well of a library of samples one after the other whereby a plurality of samples are serially loaded into the flow characterization system, and subsequently serially injected into the mobile phase of the characterization system in a plug flow fashion. Preferably, the microprocessor 222 of the auto-sampler comprises a user-interface that can be programmed to allow for variations from a normal sampling routine (e.g., skipping certain elements at certain spatial addresses of a library). The auto-sampler 200 can also be controlled for manual operation on an individual sample by sample basis.

The microprocessor 222 is also preferably user-programmable to accommodate libraries of polymer samples having varying arrangements of arrays of polymer samples (e.g., square arrays with "n-rows" by "n-columns", rectangular arrays with "n-rows" by "m-columns", round arrays, triangular arrays with "r-" by "r-" by "r-" equilateral sides, triangular arrays with "r-base" by "s-" by "s-" isosceles sides, etc., where n, m, r, and s are integers). More particularly, for example, with respect to square or rectangular arrays, a two sets of samples (e.g., libraries) having different spatial configurations can be sampled as follows. First, an auto-sampler is programmed (e.g., via a user interface module) with location information for a first set of samples comprising a plurality of samples in a plurality of sample containers in first spatial arrangement (e.g., "n-rows" by "m-columns", where n and m are integers). The first set of samples are serially withdrawn from their respective sample containers, and at least a portion of each of the withdrawn first set of samples are serially delivered to the sample-loading port of the injection system. The auto-sampler is then reprogrammed with location information for a second set of liquid samples that comprise a plurality of samples in a plurality of sample containers in second spatial arrangement (e.g., "p-rows" by "q-columns", where p and q are integers). The second set of samples are serially withdrawn from their respective sample containers, and at least a portion of each of the withdrawn second set of samples are serially delivered to the sample-loading port of the injection system.

In a preferred protocol for sampling a plurality of polymer samples, an auto-sampler provides for rapid-serial loading of the plurality of polymer samples into a common injection port of an injection valve. More specifically, a plurality of polymer samples is sampled as follows. At a first withdrawal time, $t_{Asw1}$, a first polymer sample is withdrawn from a first sample container at a first location into a probe of an auto-sampler. At least a portion of the withdrawn first sample is then delivered to an injection port of a polymer characterization system, either directly, or through a loading port and a transfer line. After delivery of the first polymer sample, a second polymer sample is, at a second withdrawal time, $t_{ASW2}$, withdrawn from a second sample container at a second location into the auto-sampler probe. At least a portion of the withdrawn second sample is then delivered (directly or indirectly) to the sample-loading port (e.g., injection port). The cycle can then be repeated, as necessary, in an automated manner, for additional samples included within the plurality of samples.

The auto-sampler cycle time, $T_{AS}$, delineated by the difference in time, $t_{Asw2} - t_{Asw1}$, is not critical, and can vary widely depending on the application of the present invention. If the parallel chromatography techniques of the present invention are applied in connection with standard, conventional HPLC systems and protocols (typically involving from about 30 minutes to about 60 minutes or more per sample), the sampling cycle time, $T_{AS}$, can range from about ten seconds to about 30 minutes or more. If, however, the parallel chromatography techniques of the invention are applied in connection with rapid-serial HPLC systems and protocols as disclosed in the above-identified co-pending applications from which the present application claims priority, (typically involving from about less than 1 minute per sample to about 10 minutes per sample), the sampling cycle time, TAS, can range from about ten seconds to about 4 minutes or more. In general, the sampling time, TAS, is preferably not more than about 10 seconds, not more than about 15 seconds, not more than about 20 seconds, not more than about 30 seconds, not more than about 1 minute, not more than about 2 minutes, not more than about 4 minutes, not more than about 8 minutes, not more than about 10 minutes, not more than about 20 minutes, or not more than about 30 minutes.

Figure 1D:
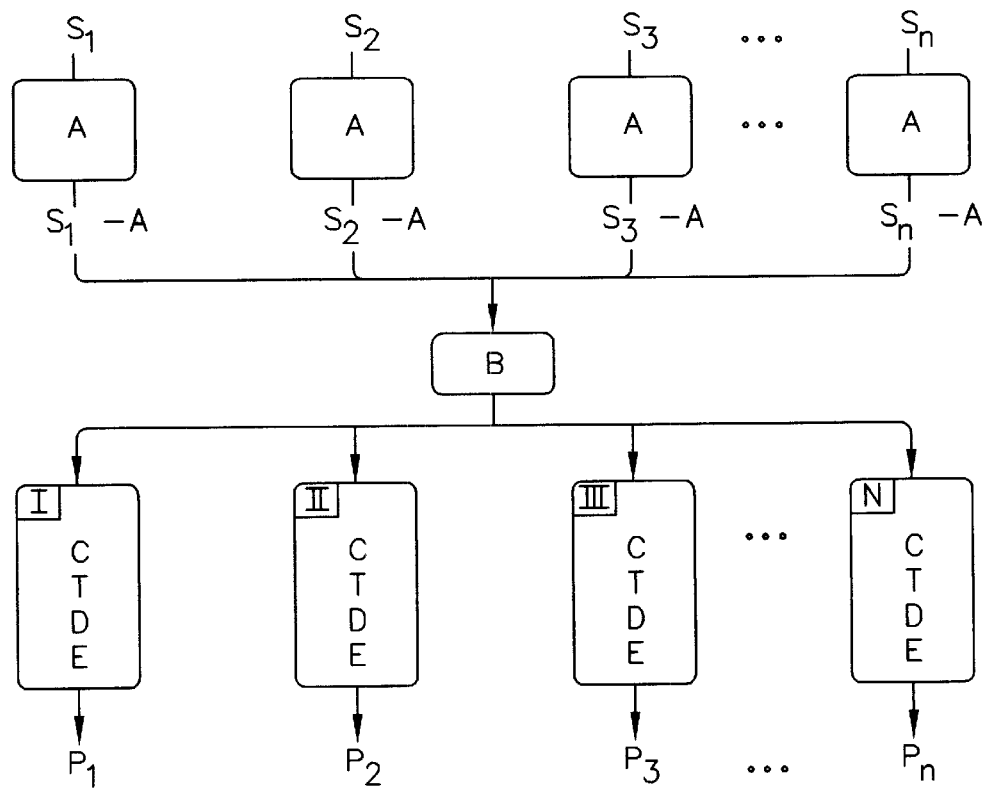
Figure 1E:
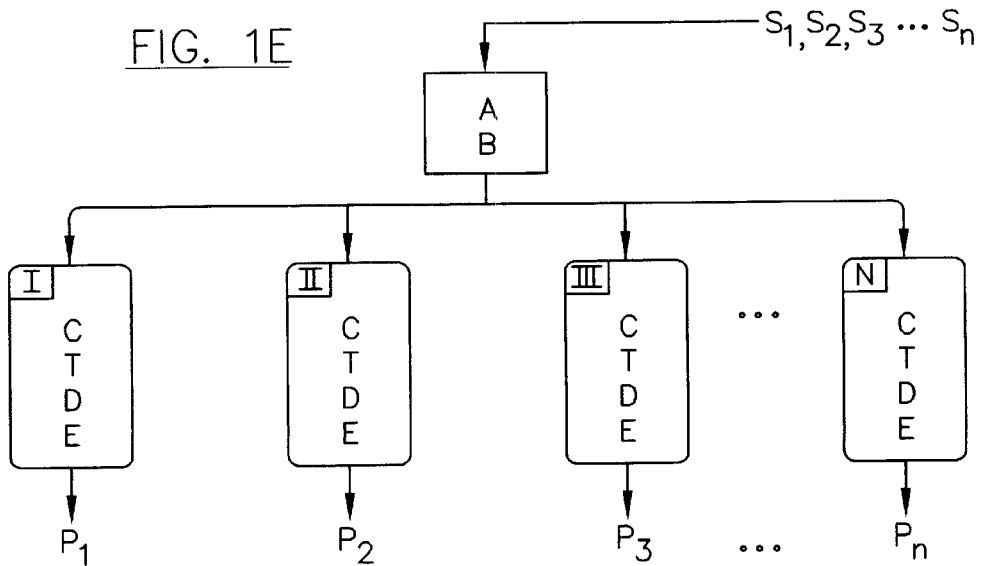
Figure 1F:
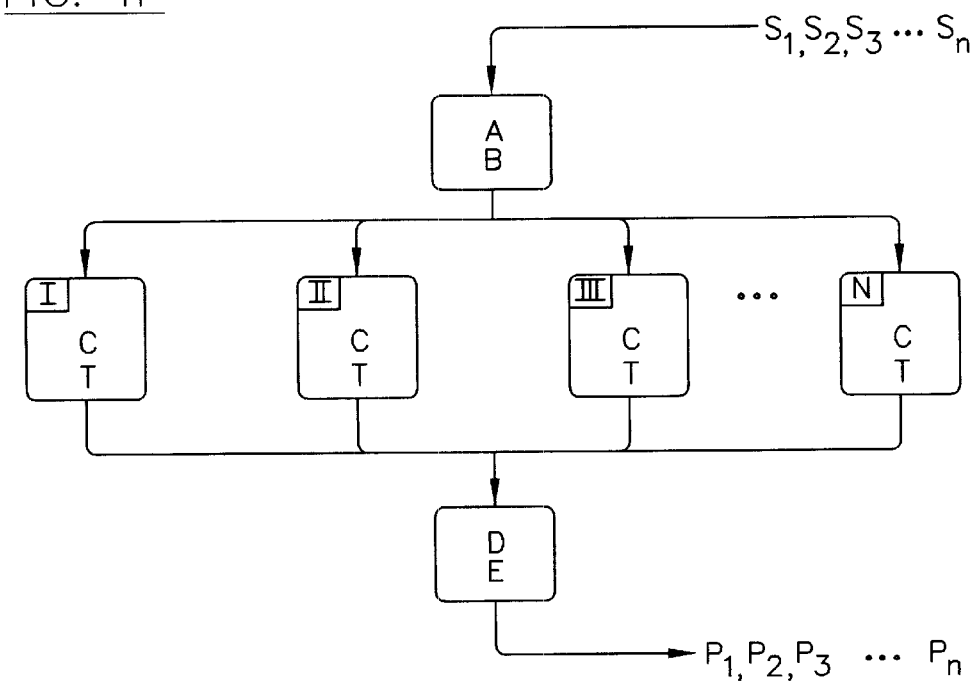
Figure 1G:
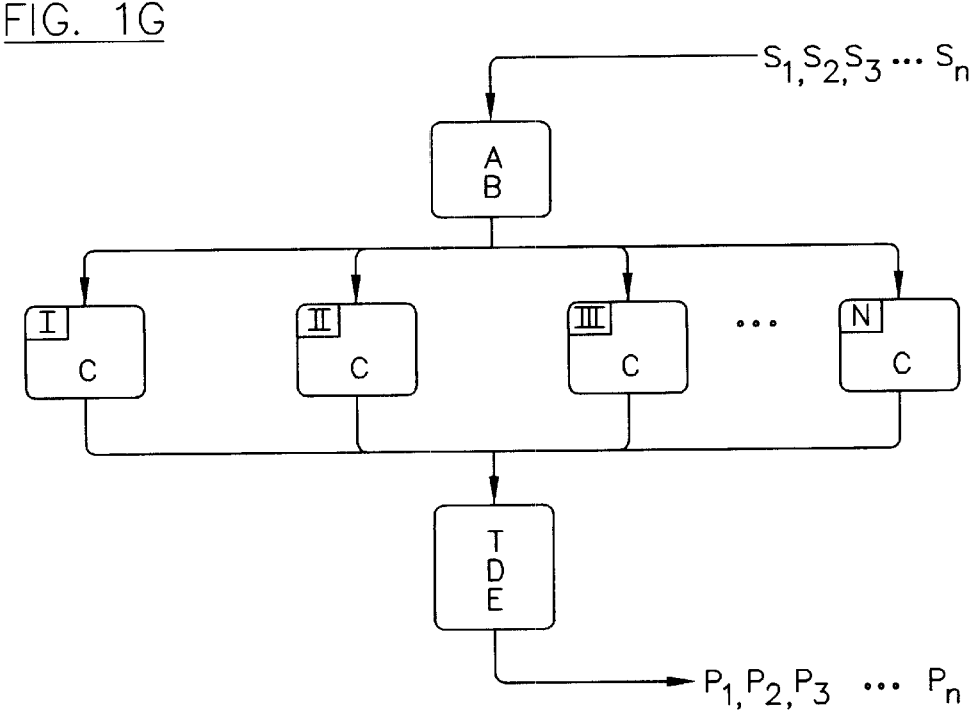

The preferred protocol for sampling a plurality of polymer samples can also include additional automated steps, as described in the above-identified cases from which the present application claims priority. In particular, sample preparation steps can be incorporated into the sampling routine. Such preparation steps can generally be effected in series with the sample loading/injection steps (See, for example, FIGS. 1B and 1C), or alternatively, can be effected in parallel with each other (FIG. 1D).

Various schemes for the timing of sample loading, injecting and distributing the serially received samples among the two or more chromatographic columns for parallel separation and subsequent treatement and detection can be employed. In general, the selection of a particular scheme can depend on factors such as the type of parallel HPLC configuration with which the treatment systems is employed, whether the treatement system is set up as a parallel treatment or serial treatment, the number of samples being characterized, the chemical diversity of samples, the number of parallel chromatographic columns in the HPLC system of the invention, the size of the columns, the separation media and separation type (e.g., GPC, precipitation-redissolution, adsorption, etc.), the configuration of the detector(s), and the detection protocols, among others. As such, a person of skill in the art will have wide latitude to vary the timing, injecting, optionally distributing, separation, treatment and detection of the plurality of samples.

The number of parallel chromatographic channels, each comprising a one or more chromatography columns in series, can generally be two or more. The number of parallel chromatographic channels (and chromatography columns) is preferably 4 or more, 8 or more, 12 or more, 16 or more, 32 or more, 48 or more, 64 or more, or 96 or more. As discussed above in connection with FIG. 4C, nested multi-port switching valves can readily accommodate such large numbers of channels.

With reference to FIGS. 2A and 2B, the chromatographic channels can also include in-line filters 104a, 104b, 104c, 104d and/or pulse dampers (not shown)—typically incorporated into the sample supply conduits 80a, 80b, 80c, 80d. The in-line filters 104 can be of any suitable dimensions and mesh size. In one embodiment, effective for screening and evaluation of polymer samples, filters 104 can retain particles having a diameter of more than about 0.5 $\mu$m. In another embodiment for polymer samples, filters 104 can retain particles having a diameter of more than about 0.2 $\mu$m. Other sizes may also be employed, as suitable for a particular sample and/or process application. Additional in-line filters can likewise be employed. While shown in FIGS. 2A and 2B immediately downstream of the connectors 84a, 84b, 84c, 84d to the injection system 90, the particular location of the filters is not critical. Moreover, the sample could be filtered as a preparation step, prior to loading of the sample into the HPLC system. Other in-line systems, such as pulse-dampers can also be employed.

After injection of a sample into a stream of liquid serving as a mobile phase of a liquid chromatography channel, the sample is introduced into a chromatographic column containing a separation medium having a stationary-phase for separation of one or more components of the sample from other components thereof. Separation is effected by selectively eluting one or more of the components from the stationary-phase with the mobile-phase acting also as an eluant. The degree of separation, also referred to as the resolution of the polymer sample components, can vary depending on the particular chemical nature of the polymer sample components, and the quality of information required in the particular characterization application. In general, the separation performance in a given case can be controlled as a function of the column design/geometry, the stationary-phase media, and the elution conditions with the mobile phase.

The particular design of a chromatographic column for liquid chromatography is, in the general case, not narrowly critical. A number of columns known in the art can be employed in connection with the present invention—as purchased or with minor variations disclosed herein. In general, with reference to FIG. 2A, the chromatographic column 102 of a liquid chromatography system 10 comprises an interior surface defining a pressurizable separation cavity having a defined volume, an inlet port for receiving a mobile phase and for supplying a polymer sample to the separation cavity, and an effluent port for discharging the mobile phase and the polymer sample or separated components thereof from the separation cavity. The separation cavity is preferably pressurizable to pressures typically involved with high-pressure liquid chromatography—such pressures generally ranging from about atmospheric pressure to about 6000 psig (about 40 MPa). In some preferred liquid-chromatography characterization methods, discussed in greater detail below, the chromatographic column can be relatively shorter, and relatively wider, compared to traditional chromatographic separation columns. Such preferred high-aspect ratio columns are disclosed in greater detail in co-pending U.S. patent application Ser. No. 09/285,393 entitled "Rapic Characterization of Polymers", filed Apr. 2, 1999 by Petro et al.

The chromatographic column 102 further comprises a separation medium having a stationary-phase within the separation cavity. The separation medium can consist essentially of a stationary-phase or can also include, in addition thereto, an inert support for the stationary phase. The column 102 can also comprise one or more fillers, frits (for separation medium retention and/or for filtering), and various fittings and features appropriate for preparing and/or maintaining the column for its intended application. The particular separation medium to be employed as the stationary-phase is not critical, and will typically depend on the separation strategy for the particular chemistry of the polymer samples of interest, as well as on the desired detection, sample-throughput and/or information quality. Typical stationary-phase media can be a bed of packed beads, rods or other shaped-particles, or a monolithic medium (typically greater than about 5 mm in thickness), each of which can be characterized and optimized for a particular separation strategy with respect to the material, size, shape, pore size, pore size distribution, surface area, solvent regain, bed homogeneity (for packed shaped-particles), inertness, polarity, hydrophobicity, chemical stability, mechanical stability and solvent permeability, among other factors. Generally preferred stationary-phase include porous media (e.g., porous beads, porous monoliths), such as are suitable for gel permeation chromatography (GPC), and media suitable for precipitation-redissolution chromatography, adsorption chromatography, and/or reverse-phase chromatography. Non-porous particles or empty columns and/or capillaries with adsorptive walls can be used as well. If beads are employed, spherical beads are preferred over other shapes. Particularly preferred stationary-phase media for polymer characterization applications are disclosed in greater detail below, but can generally include silica, cross-linked resins, hydroxylated polyglycidyl methacrylates,(e.g., poly(2-3-dihydroxypropylmethacrylate)), poly(hydroxyethyl methacrylate), and polystyrenic polymers such as poly (styrenedivinylbenzene).

The mobile-phase fluid(s) employed to elute one or more polymer components from a chromatographic stationary-phase are not generally critical, and can vary depending on the chemistry of the separation being effected. The mobile phase can be varied with respect to composition, temperature, gradient rates, flow-rates, and other factors affecting selectivity, speed of separation, peak capacity (e.g., maximum number of components that can be separated with a single run) and/or resolution of a polymer component. Exemplary mobile-phase fluids for GPC include tetrahydrofuran (THF), toluene, dimethylformamide, water, aqueous buffers, trichlorobenzene and dichlorobenzene. Exemplary mobile-phase fluids for precipitation-redissolution chromatography include THF, methanol, hexane, acetone, acetonitrile and water. For adsorption chromatography, the mobile phase can include, for example, hexane, isooctane, decane, THF, dichloromethane, chloroform, diethylether and acetone. For reverse-phase chromatography, the mobile phase can include water, acetonitrile, methanol and THF, among others.

Significantly, preferred mobile phase flow are typically faster than flowrates employed conventionally for high-pressure liquid chromatography. The flowrates can vary, depending on the separation being effected, but can, in many instances, range from about 0.1 ml/min about 25 ml/min, and preferably range from about 1 ml/min to about 25 ml/min. It may be desirable, for some detector configurations, to split off a part of the sample-containing mobile phase such that the flow rate to a particular detector is reduced to an acceptable level. For liquid chromatography systems, such a split would typically occur after the column and before the detector.

A treated sample such as a treated polymer sample (or one or more components thereof) is characterized by detecting a property of the sample, or by detecting a property of a component (e.g., a polymer component, a monomer component) of the sample. In many cases, the property is detected over a period of time, such that a variation in the property can be observed or detected or the rate of change of variation of a property can be observed or detected. In the general case, the detected property can be any property which can provide a scientifically meaningful basis of comparison between two different polymer samples or between two different polymer components—either directly, or after being correlated to a specific characterizing property of interest. The detected property can be a chemical property or a physical property of the sample or component thereof. In preferred applications, an optical property of the polymer sample or a component thereof can be detected. For example, an amount, frequency, intensity or direction of an incident light that is refracted, scattered, and/or absorbed by the polymer sample or a component thereof may be detected. Other properties, such as pressure or other factors affecting a particular characterizing property of interest (e.g., viscosity) can likewise be detected.

The detection step can be performed in parallel, in serial-parallel, or in series. With reference to FIGS. 2B and 2C, a property of a sample or of a component thereof, such as a chromatographically separated component thereof, can be detected with one or more detectors 130.

Parallel detection can be effected with two or more detectors (e.g., detectors 130a, 130b, 130c, 130d as shown in FIGS. 2A, 2B), and with each of such detectors being dedicated to one or more chromatographic channels (i.e., the flow cells of each of such detectors being in fluid communication with one or more chromatography columns). Parallel detection is particularly preferred in combination with rapid-serial techniques (e.g., overlaid injection/separation techniques) applied to any particular chromatographic column. In one preferred particular approach, parallel flow cells—each being dedicated to on chromatographic channel—are employed but the detection electronics associated therewith is electronically and serially switched between two or more of the flow cells, thereby reducing the amount of analysis circuitry required.

Serial detection can also be effected, particularly where detection is faster than the separation, and within the timing intervals for sampling, injection and switching. In one serial embodiment, shown in FIG. 2C, the parallel chromatography column effluents (e.g.,mobile phase w/separated samples) can be serially directed through a detection switching valve 60 to the flow-cell 131 of a detector 130.

In preferred embodiments, a property of a polymer sample or of a component thereof is detected with an optical detector such as a refractive-index detector, an ultraviolet-visual detector, a photodiode array detector, a static-light-scattering detector, a dynamic-light-scattering detector, and/or an evaporative-light-scattering detector—also known as an evaporative mass detector (EMD). Other detectors (e.g., a capillary viscometer detector, photodiode array detector (PDAD), infra-red detector, fluorescence detector, electrochemical detector, conductivity detector, etc.) can likewise be employed in connection with the present invention. The particular nature of the detector (eg., shape and/or configuration of a detection cavity 131 within the detector) is not generally critical.

The protocols for characterizing one or more samples preferably further comprise determining a property of interest from the detected property. The physically-detected properties, such as the capability of the sample or component thereof to refract, scatter, emit or absorb light can be correlated to properties of interest. For polymer samples, for example, such properties of interest include, without limitation, weight-average molecular weight, number-average molecular weight, viscosity-average molecular weight, peak molecular weight, approximate molecular weight, polydispersity index, molecular-weight-distribution shape, relative or absolute component concentration, chemical composition, conversion, concentration, mass, hydrodynamic radius ($R_h$), radius of gyration ($R_g$), chemical composition, amounts of residual monomer, presence and amounts of other low-molecular weight impurities in polymer samples, particle or molecular size, intrinsic viscosity, molecular shape, molecular conformation, and/or agglomeration or assemblage of molecules. The correlation between a detected property and a determined property of interest can be based on mathematical models and/or empirical calibrations. Such correlation methods are generally known in the art, and are typically incorporated into commercially-available chromatographic detectors and/or detector or data-acquisition software.

For combinatorial polymer science research applications, as well as other applications, the characterization protocols can be effected to determine at least a weight-average molecular weight as a characterization property of primary importance. Other characterization properties of interest of substantial importance, include number-average molecular weight, polydispersity index, and molecular-weight-distribution shape. For polymer samples that are polymerization product mixtures, another characterization property of substantial importance is conversion data for the polymerization reaction, typically expressed as % monomer converted into polymer. The composition of the polymer sample or of particular components thereof (e.g., polymer components) can also be of substantial importance.

For determining weight-average molecular weight from detected properties, a liquid chromatography system or a flow-injection analysis system can advantageously employ a single detector or a combination of two or more detectors. In a single-detector embodiment, for example, a dynamic light-scattering (DLS) detector can be used by itself to determine an average hydrodynamic radius or a distribution of hydrodynamic radii from the detected scattered light. The hydrodynamic radii can, in turn, be correlated to an average molecular weight or a molecular weight distribution. In a two-detector embodiment, for example, a static-light scattering (SLS) detector (where the detected scattered light is a function of weight-average molecular weight ($M_w$), concentration (C) and the square of the refractive index increment, $(dn/dC)^2$) can be combined with a refractive index (RI) detector (where the detected refracted light is a function of (C) and (dn/dC)), with an ultraviolet/visible light absorbance (UV/VIS) detector (where the detected absorbed light is a function of (C)), or with an evaporative light scattering detector (ELSD) (where the detected scattered light is a function of (C)). In another embodiment, a single-detector or multiple detectors (e.g., SLS) can detect the intensity of light scattered by the sample or sample component at two or more different angles, which can be correlated to molecular weight.

For polymer samples that are polymerization product mixtures, conversion data for the polymerization reaction of which the sample is representative can be determined by chromatographically resolving the polymer component(s) and monomer component(s), determining a molecular-weight distribution for such components, integrating areas under the respective peaks, and then comparing the integrated peak areas (e.g., using response factors for particular components and detector employed). Another approach for calculating conversion involves converting the polymer-peak area into polymer concentration or mass using a concentration-detector response calibration plot, and then comparing the portion of the polymer mass or concentration found in the sample to the expected mass or concentration assuming 100% stoichiometric conversion. Composition data for a polymer sample can be determined from the consumption of monomer or comonomers or, alternatively, from a retention time per volume of the polymer peak or a fraction thereof.

Advantageously, an ELSD detector, or other detectors that are not particularly sensitive to low-molecular weight components of a polymer sample, can be advantageously employed in connection with the flow characterization protocols of the invention to achieve a high sample-throughput. As discussed in greater detail below, detectors that are insensitive to low-molecular weight components can be advantageously employed in connection with rapid-serial overlapping techniques. Moreover, because the ELSD is also less sensitive to temperature variations than other types of mass detectors (e.g., RI detector) and is not required to be in thermal equilibrium with the sample being detected, an ELSD detector can be employed advantageously in connection with high-temperature polymer characterization systems. Hence, detecting a property of a polymer sample or a component there of with an ELSD or with other low-MW insensitive or less temperature sensitive mass detectors provides a further aspect for improving the sample throughput—particularly for a liquid chromatography system 10 or a flow-injection analysis system 20.

The aforementioned characterizing properties of interest can, once determined, be mathematically combined in various combinations to provide figures of merit for various properties or attributes of interest. In particular, for example, molecular weight, conversion and polydispersity index can be evaluated versus polymerization process time to provide mechanistic insights as to how polymers are formed. Other combinations of the fundamental characterization properties of interest will be apparent to those of skill in the art.

Specific applications and/or combinations of detectors, as well as correlation protocols, are discussed in greater detail in the above-identified co-pending U.S. applications to which the present application claims priority.

Referring to the various figures, one or more microprocessors can, as noted above, be employed for controlling every aspect of the flow characterization systems, including: the pump 116 (e.g., mobile-phase flow-rate, flow-rate gradients, compositional gradients, temperature gradients, acceleration rates for such gradients); the reservoir 114 (e.g., temperature, level); the auto-sampler 200 (e.g., movements between spatial position, timing thereof, sample selection, sample preparation, sampling pump flow-rates, and other operations), the injection valve 100 (e.g., timing, selection of sample loops, etc.); the multi-port switch 70, the column 102 (e.g., column selection (if multiple columns and automated column-switching valves are present), column temperature); the detection switch 60 (as applicable), the detector 130 (e.g. data acquisition (e.g., sampling rate), data processing (e.g., correlation); the detector parameters (e.g., wavelength); and/or overall system conditions (e.g., system pressure, temperature). Software is typically available from detector and/or liquid chromatography system manufacturers (e.g., MILLENIUM™ 2000 software available from Waters (Milford, Mass.).

Inverse Chromatography and Other Solid-Phase Interaction Evaluations

In one application, the present invention can be employed, substantially as described above, for "inverse chromatography" studies, in which the object and subject of the study are reversed as compared to "regular" chromatography. In addition, this concept can be advantageously extended to the study of other solid phase—liquid phase interactions (that may not necessarily involve separation of sample components and, as such, may not be considered to be "chromatography").

In general, a plurality of samples are serially injected into a mobile phase supplied in parallel to two or more columns, where the columns comprise solid or supported materials. The solid or supported materials can be separation media, or can be other types of solids for which there is an interest to study interactions with a mobile phase and/or vice versa. The interactions between the injected samples, or one or more components of the injected samples, and the solid or supported materials in the columns is then evaluated.

Samples

In general, the sample materials can generally comprise elements or compounds selected from the group consisting of organic materials, inorganic materials and metal-ligands. In some applications, the candidate materials will consist essentially of organic materals, consist essentially of inorganic materials, or consist essentially of metal-ligand materials. Moreover, in some applications, the sample materials will be compositions comprising mixtures of organic materials, inorganic materials and/or metal-ligand materials in the various possible combinations.

Organic materials are considered to include compounds having covalent carbon-carbon bonds. In some embodiments, the organic materials are preferably organic polymers, small-organic molecules having a molecular weight of less than about 1000, or non-biological molecules. Non-biological organic materials include organic materials other than biological materials. Biological materials are considered to include nucleic acid polymers (e.g., DNA, RNA) amino acid polymers (e.g., enzymes) and small organic compounds (e.g., steroids, hormones) where the small organic compounds have biological activity, especially biological activity for humans or commercially significant animals such as pets and livestock, and where the small organic compounds are used primarily for therapeutic or diagnostic purposes. Although in some applications the sample materials being characterized by the HPLC system are preferably not, themselves, biological organic materials, the sample materials of the invention (e.g., polymers) can be employed to prepare or separate biological organic materials. Polymeric sample materials are discussed in greater detail below.

Inorganic materials include elements (including carbon in its atomic or molecular forms), compounds that do not include covalent carbon-carbon bonds (but which could include carbon covalently bonded to other elements, e.g., $CO_2$), and compositions including elements and/or such compounds.

The samples can comprise materials that are an element, a compound or a composition comprising a plurality of elements and/or compounds. The sample materials are generally in a liquid state or are capable of being dissolved, dispersed or emulsified in a liquid phase, as appropriate for chromatographic separation (or, with respect to inverse chromatagraphy, as appropriate for the interaction between the samples and the solid or supported material.

The samples can be reaction products from a chemical reaction, which for purposes hereof, means a process in which at least one covalent bond of a molecule or compound is formed or broken. As such, immunoreactions in which immunoaffinity is based solely on hydrogen bonding or other forces—while chemical processes—are not considered to be chemical reactions. Reactions that include activation of, breaking and/or formation of H—Si, H—H, H—N, H—O, H—P, H—S, C—H, C—C, C=C, C≡C, C-halogen, C—N, C—O, C—S, C—P, C—B and C—Si bonds are exemplary. More specific exemplary chemical reactions from which reaction-product samples may derive, include, without limitation, oxidation, reduction, hydrogenation, dehydrogenation (including transfer hydrogenation), hydration, dehydration, hydrosilylation, hydrocyanation, hydroformylation (including reductive hydroformylation), carbonylation, hydrocarbonylation, arnidocarbonylation, hydrocarboxylation, hydroesterification, hydroamination, hetero-cross-coupling reaction, isomerization (including carbon-carbon double bond isomerization), dimerization, trimerization, polymerization, co-oligomerization (e.g. CO/alkene, CO/alkyne), co-polymerization (e.g. CO/alkene, CO/alkyne), insertion reaction, aziridation, metathesis (including olefin metathesis), carbon-hydrogen activation, cross coupling, Friedel-Crafts acylation and alkylation, Diels-Alder reactions, C—C coupling, Heck reactions, arylations, Fries rearrangement, vinylation, acetoxylation, aldol-type condensations, aminations, reductive aminations, epoxidations, hydrodechlorinations, hydrodesulfurations and Fischer-Tropsch reactions, asymmetric versions of any of the aforementioned reactions, and combinations of any of the aforementioned reactions in a complex reaction sequence of consecutive reactions. A combinatorial library or array comprising different reaction-product samples can be formed, for example, as the reaction product from a chemical reactions involving a library of diverse catalysts, and/or variations in reactants, coreactants, cataloreactants, selective blocking moieties, etc. As used herein, the term catalyst is intended to include a material that enhances the reaction rate of a chemical reaction of interest or that allows a chemical reaction of interest to proceed where such reaction would not substantially proceed in the absence of the catalyst.

Polymer Samples

The present invention is particularly preferred in connection with the characterization of polymer samples, and especially, combinatorial libraries comprising different polymer samples. The polymer sample can be a homogeneous polymer sample or a heterogeneous polymer sample, and in either case, comprises one or more polymer components. As used herein, the term "polymer component" refers to a sample component that includes one or more polymer molecules. The polymer molecules in a particular polymer component have the same repeat unit, and can be structurally identical to each other or structurally different from each other. For example, a polymer component may comprise a number of different molecules, with each molecule having the same repeat unit, but with a number of molecules having different molecular weights from each other (e.g., due to a different degree of polymerization). As another example, a heterogeneous mixture of copolymer molecules may, in some cases, be included within a single polymer component (e.g., a copolymer with a regularly-occurring repeat unit), or may, in other cases, define two or more different polymer components (e.g., a copolymer with irregularly-occurring or randomly-occurring repeat units). Hence, different polymer components include polymer molecules having different repeat units. It is possible that a particular polymer sample (e.g., a member of a library) will not contain a particular polymer molecule or polymer component of interest.

The polymer molecule of the polymer component is preferably a non-biological polymer. A non-biological polymer is, for purposes herein, a polymer other than an amino-acid polymer (e.g., protein) or a nucleic acid polymer (e.g., deoxyribonucleic acid (DNA)). The non-biological polymer molecule of the polymer component is, however, not generally critical; that is, the systems and methods disclosed herein will have broad application with respect to the type (e.g., architecture, composition, synthesis method or mechanism) and/or nature (e.g., physical state, form, attributes) of the non-biological polymer. Hence, the polymer molecule can be, with respect to homopolymer or copolymer architecture, a linear polymer, a branched polymer (e.g., short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule. The particular composition of the non-biological polymer molecule is not critical, and can include repeat units or random occurrences of one or more of the following, without limitation: polyethylene, polypropylene, polystyrene, polyolefin, polyimide, polyisobutylene, polyacrylonitrile, poly(vinyl chloride), poly(methyl methacrylate), poly(vinyl acetate), poly(vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, and polyacetals. Polysaccharides are also preferably included within the scope of non-biological polymers. While some polysaccharides are of biological significance, many polysaccharides, and particularly semi-synthetic polysaccharides have substantial industrial utility with little, if any biological significance. Exemplary naturally-occurring polysaecharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

In typical applications, a polymer sample is a heterogeneous sample comprising one or more polymer components, one or more monomer components and/or a continuous fluid phase. In copolymer applications, the polymer sample can comprise one or more copolymers, a first comonomer, a second comonomer, additional comonomers, and/or a continuous fluid phase. The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, control agents, plasticizers, cosolvents and/or accelerators, among others. The various components of the heterogeneous polymer sample can be uniformly or non-uniformly dispersed in the continuous fluid phase.

The polymer sample is preferably a liquid polymer sample, such as a polymer solution, a polymer emulsion, a polymer dispersion or a polymer that is liquid in the pure state (i.e., a neat polymer). A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being a emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 2 nm to about 500 nm, more typically from about 20 nm to about 400 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2

μm to about 1000 μm, more typically from about 0.4 μm to about 500 μm, and even more typically from about 0.5 μm to about 200 μm. Exemplary polymers that can be in the form of neat polymer samples include dendrimers, and siloxane, among others. The liquid polymer sample can also be employed in the form of a slurry, a latex, a microgel a physical gel, or in any other form sufficiently tractable for analysis as described and claimed herein. Liquid samples are useful in the automated sample-handling tools that prepare and automatically sample each member of a polymer library. Liquid samples also allow the sample to flow in the chromatographic system or characterization system. In some cases, polymer synthesis reactions (i.e., polymerizations) directly produce liquid samples. These may be bulk liquid polymers, polymer solutions, or heterogeneous liquid samples such as polymer emulsions, latices, or dispersions. In other cases, the polymer may be synthesized, stored or otherwise available for characterization in a non-liquid physical state, such as a solid state (e.g., crystalline, semi-crystalline or amorphous), a glassy state or rubbery state. Hence, the polymer sample may need to be dissolved, dispersed or emulsified to form a liquid sample by addition of a continuous liquid-phase such as a solvent. The polymer sample can, regardless of its particular form, have various attributes, including variations with respect to polarity, solubility and/or miscibility.

In preferred applications, the polymer sample is a polymerization product mixture. As used herein, the term "polymerization product mixture" refers to a mixture of sample components obtained as a product from a polymerization reaction. An exemplary polymerization product mixture can be a sample from a combinatorial library prepared by polymerization reactions, or can be a polymer sample drawn off of an industrial process line. In general, the polymer sample may be obtained after the synthesis reaction is stopped or completed or during the course of the polymerization reaction. Alternatively, samples of each polymerization reaction can be taken and placed into an intermediate array of vessels at various times during the course of the synthesis, optionally with addition of more solvent or other reagents to arrest the synthesis reaction or prepare the samples for analysis. These intermediate arrays can then be characterized at any time without interrupting the synthesis reaction. It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated. The polymerization scheme and/or mechanism by which the polymer molecules of the polymer component of the sample are prepared is not critical, and can include, for example, reactions considered to be addition polymerization, condensation polymerization, step-growth polymerization, and/or chain-growth polymerization reactions. Viewed from another aspect, the polymerization reaction can be an emulsion polymerization or a dispersion polymerization reaction. Viewed more specifically with respect to the mechanism, the polymerization reaction can be radical polymerization, ionic polymerization (e.g., cationic polymerization, anionic polymerization), and/or ringopening polymerization reactions, among others. Non-limiting examples of the foregoing include, Ziegler-Natta or Kaminsky-Sinn reactions and various copolymerization reactions. Polymerization product mixtures can also be prepared by modification of a polymeric starting materials, by grafting reactions, chain extension, chain scission, functional group interconversion, or other reactions.

The sample size is not narrowly critical, and can generally vary, depending on the particular characterization protocols and systems used to characterize the sample or components thereof. Typical sample sizes can range from about 0.1 μl to about 1 ml, more typically from about 1 μl to about 1000 μl, even more typically from about 5 μl to about 100 μl, and still more typically from about 10 μl to about 50 μl. A generally preferred sample size for flow characterization systems and, particularly for liquid chromatography, is a sample size of about 20 μl.

The polymer sample, such as a polymerization product mixture, can be a raw, untreated polymer sample or can be pretreated in preparation for characterization. Typical sample preparation steps include preliminary, non-chromatographic separation of one or more components of a polymer sample from other components, dilution, mixing and/or redissolution (e.g., from a solid state), among other operations. Preliminary separation methods can help remove large-scale impurities such as dust, coagulum or other impurities. Such separation methods can include, for example: filtering (e.g. with a microfilter having pore sizes that allow the passage of particles less than about 0.5 μm or 0.2 μm); precipitation of polymer components, monomer components and/or other smallmolecule components, decanting, washing, scavenging (e.g. with drying agents), membrane separation (e.g., diafiltration, dialysis), evaporation of volatile components and/or ion-exchange. The sample is preferably diluted, if necessary, to a concentration range suitable for detection. For typical liquid chromatography applications, for example, the sample concentration prior to loading into the liquid chromatography system can range from about 0.01 mg/ml to a neat sample, more typically from about 0.01 mg/ml to about 100 mg/ml, and even more typically from about 0.1 mg/ml to about 50 mg/ml. More specific concentration ranges typical for liquid chromatography samples include from about 0.1 mg/ml to about 20 mg/ml, and from about 0.5 mg/ml to about 5 mg/ml. For flow-injection analysis systems, in which the sample is detected without substantial chromatographic separation thereof, much more dilute solutions can be employed. Hence, the concentration can range from a detectable concentration level (for the particular detector employed) up to about 1 mg/ml, or more in some applications. Typical concentrations can be about $1 \times 10^{-2}$ wt. %, about $1 \times 10^{-3}$ wt. % or about $1 \times 10^{-4}$ wt. %. Mixing can be required to increase the uniformity of a polymer sample emulsion or dispersion, and/or to integrate one or more additional components into the polymer sample. Preparation steps, and particularly rapid preparation techniques, can be an important aspect for combinatorial polymer investigations—since polymer samples may be synthesized in a form not ideally suited for immediate characterization.

Non-Polymer Samples

Although the primary applications of the present invention are directed to combinatorial polymer science research and/or quality control for industrial polymer synthesis or processing protocols, aspects of the invention can have applications involving non-polymer samples. A non-polymer sample can be a material that comprises an organic or an inorganic non-polymer element or compound. Oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for a biological field (e.g., steroids, hormones, etc.). More particularly, such non-biological, non-polymer elements or compounds can include organic or inorganic materials such as pigments, carbon powders (e.g., carbon black), metals, metal oxides, metal salts, metal colloids, metal ligands, etc, without particular limitation.

Pluralities of Samples/Libraries of Samples

A plurality of samples such as polymer samples comprises 2 or more samples that are physically or temporally separated from each other—for example, by residing in different sample containers, by having a membrane or other partitioning material positioned between samples, by being partitioned (e.g., in-line) with an intervening fluid, by being temporally separated in a flow process line (e.g., as sampled for process control purposes), or otherwise. The plurality of samples preferably comprises 4 or more samples, more preferably 8 or more samples, and even more preferably 10 or more samples. Four samples can be employed, for example, in connection with experiments having one control sample and three polymer samples varying (e.g. with respect to composition or process conditions as discussed above) to be representative of a high, a medium and a low-value of the varied factor—and thereby, to provide some indication as to trends. Eight samples can provide for additional variations in the explored factor space. Moreover, eight samples corresponds to the number of parallel polymerization reactors in the PPR-8™, being selectively offered as one of the Discovery Tools™ of Symyx Technologies, Inc. (Santa Clara, Calif.). Higher numbers of samples can be investigated, according to the methods of the invention, to provide additional insights into larger compositional and/or process space. In some cases, for example, the plurality of samples can be 15 or more samples, preferably 20 or more samples, more preferably 40 or more samples and even more preferably 80 or more samples. Such numbers can be loosely associated with standard configurations of parallel reactor configurations (e.g., the PPR-48™, Symyx Technologies, Inc.) and/or of standard sample containers (e.g. 96-well microtiter plate-type formats). Moreover, even larger numbers of samples such as polymer samples can be characterized according to the methods of the present invention for larger scale research endeavors. Hence, the number of samples can be 150 or more, 400 or more, 500 or more, 750 or more, 1,000 or more, 1,500 or more, 2,000 or more, 5,000 or more and 10,000 or more polymer samples. As such, the number of samples can range from about 2 samples to about 10,000 samples, and preferably from about 8 samples to about 10,000 samples. In many applications, however, the number of samples can range from about 80 samples to about 1500 samples. In some cases, in which processing of samples using typical 96-well microtiter-plate formatting is convenient or otherwise desirable, the number of samples can be 96*N, where N is an integer ranging from about 1 to about 100. For many applications, N can suitably range from 1 to about 20, and in some cases, from 1 to about 5.

The plurality of samples can be a combinatorial library of samples. A library of samples comprises of two or more different samples, and can be in an array format as spatially separated samples—preferably on a common substrate, or temporally separated—for example, in a flow system. Candidate samples (i.e., members) within a library may differ in a definable and typically predefined way, including with regard to chemical structure, processing (e.g., synthesis) history, mixtures of interacting components, purity, etc. The samples can be spatially separated, preferably at an exposed surface of the substrate, such that the array of samples are separately addressable for sampling into the characterization system and subsequent characterization thereof. The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. Typically, however, for combinatorial polymer science research applications, at least two or more, preferably at least four or more, even more preferably eight or more and, in many cases most, and allowably each of the plurality of polymer samples in a given library of polymer samples will be different from each other. Specifically, a different polymer sample can be included within at least about 50%, preferably at least 75%, preferably at least 80%, even more preferably at least 90%, still more preferably at least 95%, yet more preferably at least 98% and most preferably at least 99% of the polymer samples included in the sample library. In some cases, all of the polymer samples in a library of polymer samples will be different from each other.

The substrate can be a structure having a rigid or semi-rigid surface on which or into which the array of polymer samples can be formed or deposited. The substrate can be of any suitable material, and preferably consists essentially of materials that are inert with respect to the polymer samples of interest. Certain materials will, therefore, be less desirably employed as a substrate material for certain polymerization reaction process conditions (e.g., high temperatures—especially temperatures greater than about 100° C. or high pressures) and/or for certain reaction mechanisms. Stainless steel, silicon, including polycrystalline silicon, single-crystal silicon, sputtered silicon, and silica ($SiO_2$) in any of its forms (quartz, glass, etc.) are preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Organic and inorganic polymers may also be suitably employed in some applications of the invention. Exemplary polymeric materials that can be suitable as a substrate material in particular applications include polyimides such as Kapton™, polypropylene, polytetrafluoroethylene (PTFE) and/or polyether etherketone (PEEK), among others. The substrate material is also preferably selected for suitability in connection with known fabrication techniques. As to form, the sample containers formed in, at or on a substrate can be preferably, but are not necessarily, arranged in a substantially flat, substantially planar surface of the substrate. The sample containers can be formed in a surface of the substrate as dimples, wells, raised regions, trenches, or the like. Non-conventional substate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications. In preferred embodiments, the substrate is designed such that the individually addressable regions of the substrate can act as polymerization reaction vessels for preparing a polymerization product mixture (as well as sample containers for the two or more different polymer samples during subsequent characterization thereof. Glass-lined, 96-well, 384-well and 1536-well microtiter-type plates, fabricated from stainless steel and/or aluminum, are preferred substrates for a library of polymer samples. The choice of an appropriate specific substrate material and/or form for certain applications will be apparent to those of skill in the art in view of the guidance provided herein.

The library of polymer materials can be a combinatorial library of reaction product mixtures such as polymerization product mixtures. Polymer libraries can comprise, for example, polymerization product mixtures resulting from polymerization reactions that are varied with respect to, for example, reactant materials (e.g. monomers, comonomers), catalysts, catalyst precursors, initiators, additives, the relative amounts of such components, reaction conditions (e.g., temperature, pressure, reaction time) or any other factor affecting polymerization. Design variables for polymerization reactions are well known in the art. See generally, Odian, *Principles of Polymerization*, 3$^{rd}$ Ed., John Wiley & Sons, Inc. (1991). A library of polymer samples may be prepared in arrays, in parallel polymerization reactors or in a serial fashion. Exemplary methods and apparatus for preparing polymer libraries—based on combinatorial polymer synthesis approaches—are disclosed in copending U.S. patent application Ser. No. 09/211,982 of Turner et al filed Dec. 14, 1998, copending U.S. patent application Ser. No. 09/227,558 of Turner et al. filed Jan. 8, 1999, copending U.S. patent application Ser. No. 09/235,368 of Weinberg et al. filed Jan. 21, 1999, and copending U.S. provisional patent application Ser. No. 60/122,704 entitled "Controlled, Stable Free Radical Emulsion and Water-Based Polymerizations", filed Mar. 9, 1999 by Klaemer et al. under Attorney Docket No. 99-4. See also, PCT Patent Application WO 96/11878.

The libraries can be advantageously characterized directly, without being isolated, from the reaction vessel in which the polymer was synthesized. Thus, reagents, catalysts or initiators and other additives for making polymers may be included with the polymer sample for characterization or screening.

While such methods are preferred for a combinatorial approach to polymer science research, they are to be considered exemplary and non-limiting. As noted above, the particular polymer samples characterized according to the methods and with the apparatus disclosed herein can be from any source, including, but not limited to polymerization product mixtures resulting from combinatorially synthesis approaches.

Mini-and Micro-Scale Applications

The methods of the present invention can be applied in connection with "normal" scale HPLC systems, and can also be applied to smaller scale systems—including particularly mini-scale systems and micro-scale systems. As used herein, mini-scale systems are considered to include those having mobile-phase supply conduits with a diameter ranging from about 3 mm to about 500 µm and micro-scale systems are considered to include those having mobile-phase supply conduits with a diameter of about 500 µm or less. Corresponding dimensions, in terms of hydraulic radius can be considered for other than circular cross-sectional areas.

The following examples further exemplify the invention. They should be considered non-limiting.

EXAMPLE 1

The Chromatographic Flow injection system was equipped with a pump and autosampler (Alliance sytem 2690, Waters), and a chromatographic column (or filter). The mobile phase coming out of the Chromatographic/Flow injection system went through the mixer into the photodiode array detector (Model 996, Waters), set up to measure absorbance at 350 nm. Another pump (Model 515, Waters) for pumping a derivatization/precipitation agent from a prepared container to the mixer was connected.

EXAMPLE 2

In the first experiment of this example, 10 □L of the solution of the narrow polyisobutylene standard (pib1100, Mw=1,110,000) from Polymer Standard Service was injected (volume) into the system with a metal filter holder with a 0.5 □m pore size frit (Valco) connected instead of separation column. Tetrahydrofuran at 1 mL/min was used as a mobile phase. No derivatization/precipitation agent was pumped into the mixer at this time. The data were acquired for 2 minutes. No significant response was seen under these conditions.

In the second experiment, the procedure was repeated as described above; however, methanol at 1 mL/min was mixed with the mobile phase coming out of the Chromatographic/Flow injection system using the mixer inserted between the system and detector. Significantly large peak was observed on the chromatogram.

In the third experiment, the procedure was repeated again using water at 0.2 mL/min as the precipitation/derivatization agent instead of methanol. Here again, significantly large peak was observed on the chromatogram.

All three chromatographic traces are shown in FIG. 6. The example clearly demostrates that adding the precipitation/derivatization agent makes previously invisible polymers visible. The wavelength from the visual light range has been chosen to demostrate ability to detect polymer in a very efficient way using optical detection system that may use even visual light. Such a detector can be very easy and cheap to build since it wouldn't require any complicated light sources and wavelength filtering.

EXAMPLE 3

In this example, water at 0.1 mL/min was used as the precipitation/derivatization agent and all the other experimental conditions were the same as those described in the Example 2.

First, three naitow polyisobutylene standards differing in molecular weights (Mw 1.1M; Mw 355 k; and 10 k, Polymer Standard Service) were injected subsequently into the system. All three polymers gave a significant detector response as compared to the blank experiment with no injection (FIG. 7A).

Then, three narrow polystyrene standards differing in molecular weights (Mw 3M; Mw 215 k; and 11 k, Polymer Laboratories) were injected subsequently into the system. No detector response was observed after injecting these standards (FIG. 7B). This example demonstrates that under certain conditions the detection can be group selective and allow us to distinguish one group of polymers from the others based on the differences in the chemical compositions.

EXAMPLE 4

In this example, a separation column (PL-gel MiniMix-D, 250×4.6 mm, 5 □m; Polymer Laboratories) was used instead of the filter, and water at various flow rates was applied as the precipitation/derivatization agent. The data were collected for 6 min per injection. All the other experimental conditions were the same as those described in the Example 2.

Figure 8A:
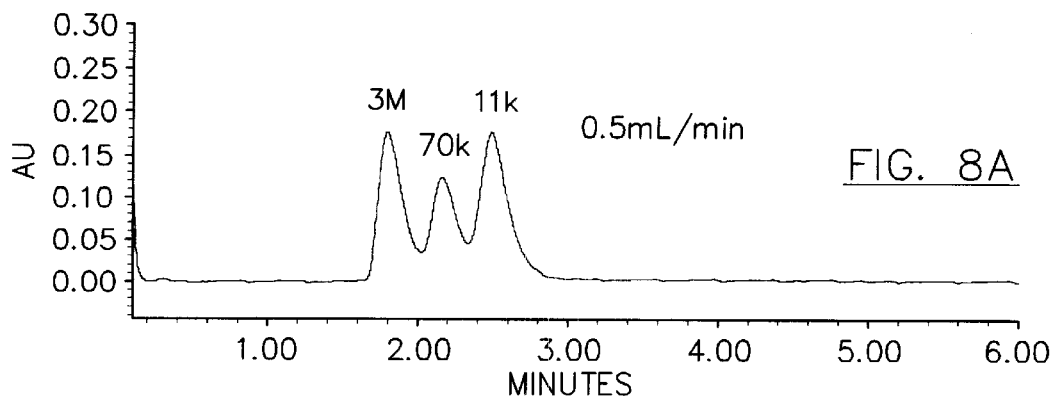
FIG. 8A through FIG. 8D are graphs of detector output (mv, absorbance at 350 nm) versus time (minutes) illustrating the results from a HPLC separation of narrow polydispersity polystyrene (PS) standards of various molecular weights (3M, 70 k and 11 k) each in a tetrahydrofuran mobile phase/eluant, run with various treatments of the chromatographic column effluent: with water at a flow rate of 0.5 ml/min (FIG. 8A); with water at a flow rate of 0.3 ml/min (FIG. 8B); with water at a flow rate of 0.15 ml/min (FIG. 8C); and with water at a flow rate of 0.1 ml/min (FIG. 8D) (See Example 3).
Figure 8B:
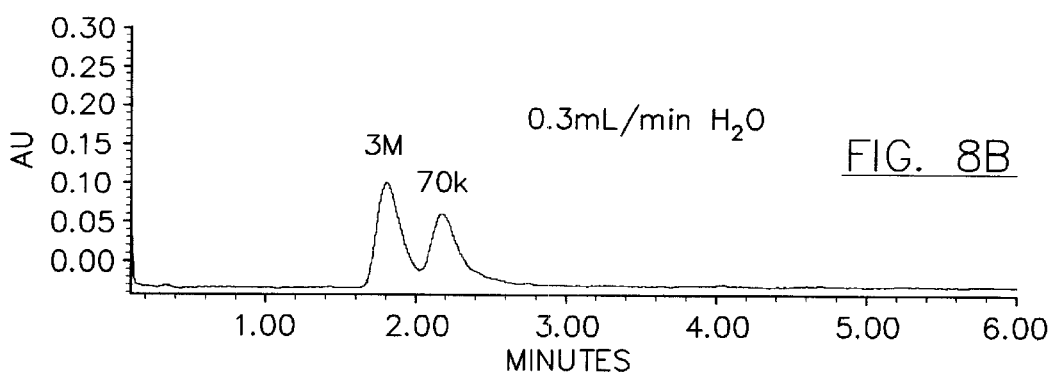
Figure 8C:
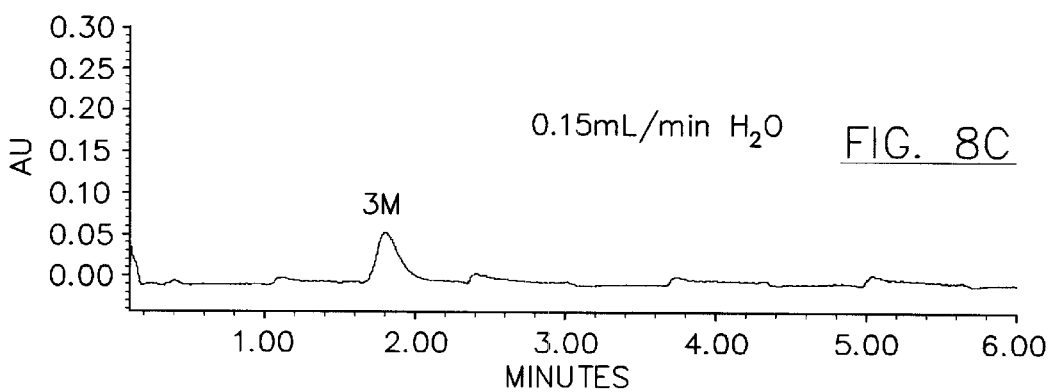
Figure 8D:
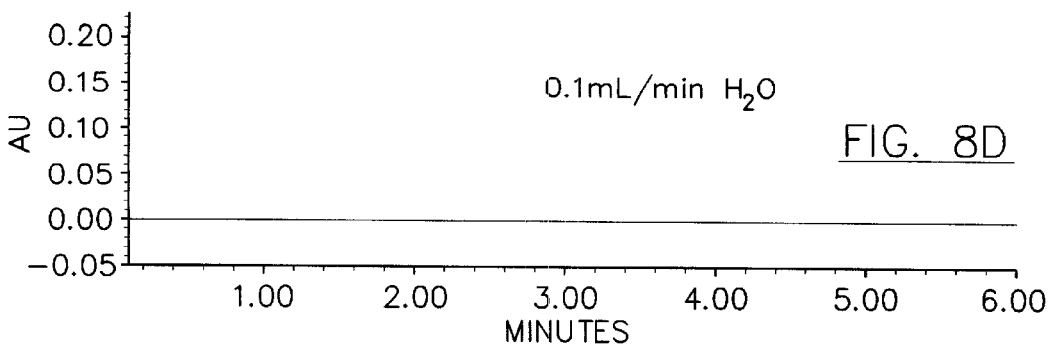

In the first experiment, a mixture of three narrow polystyrene standards differing in molecular weights (Mw 3M; Mw 70 k; and 11 k, Polymer Laboratories) was injected into the system having mobile phase coming out of the Chromatographic/Flow injection system mixed with water pumped into the mixer at 0.1 mL/min. No detector response was observed under these conditions (FIG. 8D).

In the second experiment, the same mixture of polystyrene standards was injected into the system with water at 0.15 mL/min used as the precipitation/derivatization agent. Only a peak of the polystyrene standard having the highest molecular weight (3M) was observed (FIG. 8C).

In the third experiment, the same mixture of standards was injected into the system with water at 0.3 mL/min used as the precipitation/derivatization agent. Two peaks corresponding to the two polystyrene standard having molecular weight of 3M and 70 k appeared on the chromatogram (FIG. 8B).

In the fourth experiment, the same mixture of standards was injected into the system with water at 0.5 mL/min used as the precipitation/derivatization agent. Three peaks corresponding to all of the injected polystyrene standard (3M, 70 k, 11 k) appeared on the chromatogram obtained under these conditions (FIG. 8A).

This example demonstrates that under certain conditions the detection can be molecular weight selective and allow us to distinguish polymers of the same chemical composition but of different molecular weights.

EXAMPLE 5

In this example, a separation column (PL-gel MiniMix-D, 250×4.6 mm, 5□m; Polymer Laboratories) was used instead of the filter, and either no precipitation/derivatization agent or water at 0.4 mL/min was applied to influence the detection. UV absorbance (photodiode array detector, Model 996, Waters, set up to absorbance detection at 254 nm) and Light-Scattering at 90° (MiniDawn, Wyatt Technologies) detectors were used in a series for the following experiments. The data were collected for 5 min per injection. All the other experimental conditions were the same as those described in the Example 2.

Figure 9A:
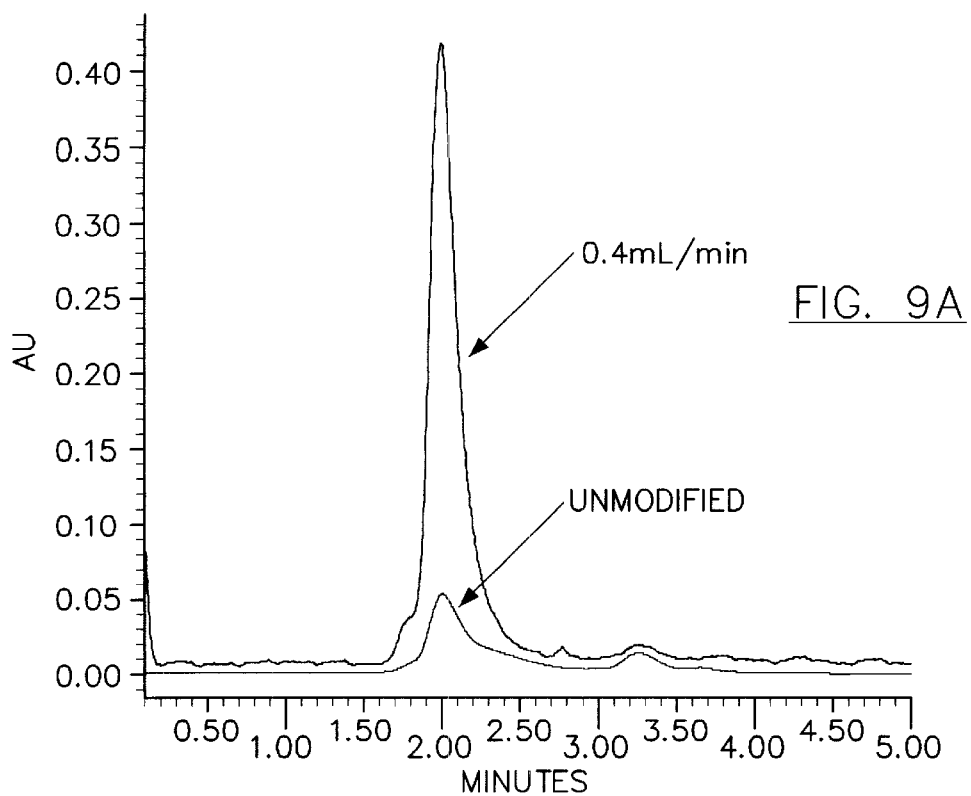
FIG. 9A and FIG. 9B are graphs of detector output (mv) versus time (minutes) with detector output be based on UV absorbance at 254 nm (FIG. 9A) or static light scattering (SLS) at 90° (FIG. 9B), illustrating the results from a HPLC separation of narrow polydispersity polystyrene (PS) standard having a molecular weight of 214 k in a tetrahydrofuran mobile phase/eluant, run: (i) without treatment of the chromatographic column effluent (unmodified control) and (ii) with treatment of the chromatographic column effluent with water at a flow rate of 0.4 ml/min (See Example 4). The detector responses are in the same scale for both overlaid traces of each figure.
Figure 9B:
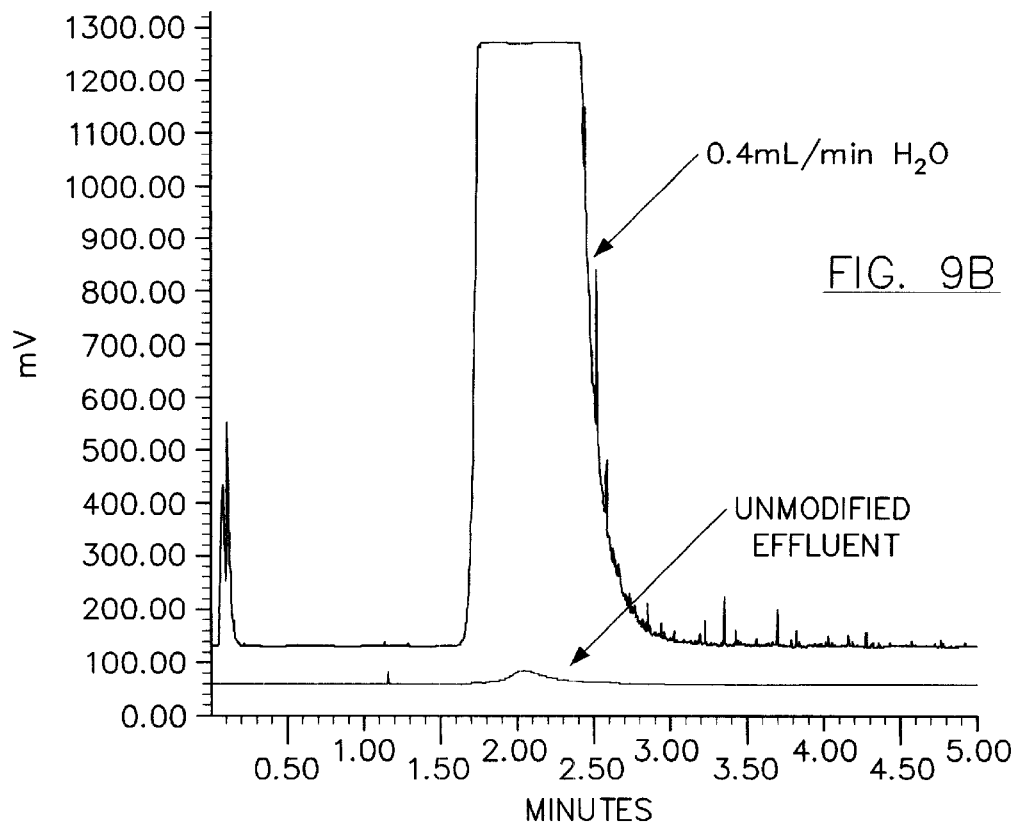

First, the narrow polystyrene standard of 214 k was injected into the system with no precipitation/derivatization agent. A response was observed on both UV detectors. Then, the injection was repeated into the system with water at 0.4 mL/min applied as precipitation/derivatization agent. Much stronger response was observed on both UV (FIG. 9A) and LS (FIG. 9B) detectors.

This demonstrates that such a post column treatment can greatly enhance the detection of polymers using various optical detection systems. This may have a vast applicability for detecting a trace amount of polymers which would he otherwise far below the sensitivity limit of a detector. Also, changing the derivatization/precipitation conditions allow to tune up the sensitivity of the detection in order to fit a large variety of concentrations within in a diverse library of polymer samples.

In light of the detailed description of the invention and the examples presented above, it can be appreciated that the several objects of the invention are achieved. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present nvention as set forth are not intended as being exhaustive or limiting of the invention.

I claim:

1. A method for characterizing a plurality of polymer samples with a liquid chromatography system, the method comprising supplying a mobile phase in parallel through each of first and second chromatographic columns of a liquid chromatography system, injecting first and second polymer samples into the mobile phase of the first and second chromatographic columns, respectively, separating at least one sample component of the injected first and second samples from other sample components thereof in the respective chromatographic columns, treating the at least one separated sample component of the first and second samples to change a property of at least one separated sample component thereof, and detecting a property of the treated sample component of the first and second samples.

2. The method of claim 1 wherein the at least one separated sample component of the first and second samples are treated to change an optical property thereof, and the detected property of the treated sample component is an optical property.

3. The method of claim 1 wherein treating comprises precipitating the at least one separated sample component.

4. The method of claim 1 wherein treating comprises selectively precipitating the at least one separated sample component.

5. The method of claim 1 wherein the samples are polymer samples, and treating comprises precipitating the at least one separated sample component by combining the chromatographic eluant with a non-solvent for the at least one separated sample component.

6. The method of claim 1 wherein the samples are polymer samples, and treating comprises precipitating the at least one separated sample component by controlling the temperature of the chromatographic eluant.

7. The method of claim 1 wherein treating comprises derivatizing the at least one separated sample component.

8. The method of claim 1 wherein treating comprises selectively derivatizing the at least one separated sample component.

9. The method of claim 1 wherein at least two or more sample components of the injected first and second samples are separated from each other and from other components thereof.

10. The method of claim 1 wherein the at least one separated sample component of the first and second samples is treated to be selectively detectable over one or more other sample components thereof, and a property of the treated sample is selectively detected thereover.

11. The method of claim 1 wherein ten or more samples are injected into the mobile phase of the first and second chromatographic columns.

12. The method of claim 1 wherein forty or more samples are injected into the mobile phase of the first and second chromatographic columns.

13. The method of claim 1 wherein eighty or more samples are injected into the mobile phase of the first and second chromatographic columns.

14. The method of claim 1 wherein 96*N samples are injected into the mobile phase of the first and second chromatographic columns, where N is an integer ranging from 1 to 5.

15. The method of claim 1 wherein ten or more different samples are injected into the mobile phase of the first and second chromatographic column.

16. The method of claim 1 wherein a property of at least one of the separated sample components of the first and second samples is detected with an optical detector.

17. The method of claim 1 further comprising determining a property of interest.

18. A method for characterizing a plurality of polymer samples with a liquid chromatography system, the method comprising supplying a mobile phase in parallel through each of first and second chromatographic columns of a liquid chromatography system, injecting first and second polymer samples into the mobile phase of the first and second chromatographic columns, respectively, separating at least one sample component of the injected first and second polymer samples from other sample components thereof in the respective chromatographic columns, precipitating or derivatizing at least one separated sample component of the first and second polymer samples, and detecting an optical property of a precipitated or derivatized sample component of the first and second polymer samples.

19. A method for characterizing a plurality of polymer samples with a liquid chromatography system, the method comprising supplying a mobile phase in parallel through each of two or more chromatographic columns of a liquid chromatography system, the mobile phase comprising a solvent for ten or more polymer samples of interest, injecting the ten or more different polymer samples of interest into the mobile phase of the two or more chromatographic columns, separating at least one sample component of the injected ten or more polymer samples from other sample components thereof in the respective chromatographic columns, combining the eluant of the chromatographic column with a non-solvent for the ten or more polymer samples of interest to precipitate the at least one separated sample component thereof, and detecting an optical property of the precipitated sample component of the ten or more polymer samples.

20. A method for characterizing a plurality of polymer samples with a liquid chromatography system, the method comprising supplying a mobile phase in parallel through each of first and second chromatographic columns of a liquid chromatography system, injecting first and second polyer samples into the mobile phase of the first and second chromatographic columns, respectively, separating at least one sample component of the injected first and second samples from one or more other sample components thereof in the respective chromatographic columns, controlling the composition or the temperature of the mobile-phase after chromatographic separation, such that an optical property of one or more of the separated sample components of the first and second samples is selectively changed relative to the optical properties of other sample components of the first and second samples, and selectively detecting the changed optical property of the at least one separated sample component of the first and second samples.

21. A method for characterizing a plurality of samples with a flow-injection analysis system, the method comprising supplying a mobile phase in parallel through each of first and second flow detectors of a flow-injection analysis system, injecting first and second polymer samples into the mobile phase of the first and second flow detectors, respectively, controlling the composition, the flow-rate or the temperature of the mobile-phase after injection of the first and second polymer samples, such that an optical property of one or more of the sample components of the first and second polymer samples is selectively changed relative to the optical properties of other sample components of the first and second polymer samples, and selectively detecting the changed optical property of the at least one sample component of the first and second polymer samples.

22. The method of claim 1, 18, 19, 20, or 21 wherein a property of at least one of the separated sample components of the first and second samples is detected in series.

23. The method of claim 1, 18, 19, 20, or 21 wherein a property of at least one of the separated sample components of the first and second samples is detected in parallel.

* * * * *

UNITED STATES PATENT AND TRADEMARK OFFICE
CERTIFICATE OF CORRECTION

PATENT NO.    : 6,436,292 B1                                     Page 1 of 1
DATED         : August 20, 2002
INVENTOR(S)   : Petro, Miroslav It is certified that error appears in the above-identified patent and that said Letters Patent is hereby corrected as shown below:

<u>Column 32,</u>
Line 7, "polyer" should be replaced with -- polymer --
Lines 46 and 49, an -- s -- should be inserted at the end of the word "claim"

Signed and Sealed this

Twenty-fifth Day of February, 2003

JAMES E. ROGAN
*Director of the United States Patent and Trademark Office*